(12) United States Patent
Neumann et al.

(10) Patent No.: US 7,407,645 B2
(45) Date of Patent: Aug. 5, 2008

(54) BIOCONJUGATES OF METAL COMPLEXES OF NITROGEN-CONTAINING MACROCYCLIC LIGANDS

(75) Inventors: William L. Neumann, Ballwin, MO (US); Dennis P. Riley, Chesterfield, MO (US); Randy H. Weiss, St. Louis, MO (US); Susan L. Henke, Webster Groves, MO (US); Patrick J Lennon, Webster Groves, MO (US); Karl W. Aston, Pacific, MO (US)

(73) Assignee: Metaphore Pharmaceuticals, Inc., St. Louis, MO (US)

( * ) Notice: Subject to any disclaimer, the term of this patent is extended or adjusted under 35 U.S.C. 154(b) by 0 days.

(21) Appl. No.: 10/737,486

(22) Filed: Dec. 16, 2003

(65) Prior Publication Data
US 2004/0131550 A1 Jul. 8, 2004

Related U.S. Application Data

(62) Division of application No. 10/405,044, filed on Apr. 1, 2003, now abandoned, which is a division of application No. 08/698,631, filed on Aug. 16, 1996, now abandoned.

(60) Provisional application No. 60/002,394, filed on Aug. 17, 1995.

(51) Int. Cl.
A61K 51/00 (2006.01)
A61M 36/14 (2006.01)
(52) U.S. Cl. .................. 424/1.73; 424/1.11; 424/1.65; 424/1.49; 424/1.69; 540/450
(58) Field of Classification Search ................ 424/9.36, 424/9.363, 9.364, 9.365, 9.361, 1.65, 1.11, 424/9.1, 1.73, 1.37, 1.47, 1.69, 1.53; 540/465, 540/473, 474
See application file for complete search history.

(56) References Cited

U.S. PATENT DOCUMENTS

| | | | |
|---|---|---|---|
| 3,930,867 A | 1/1976 | Bigelow | |
| 4,001,212 A | 1/1977 | Richman | |
| 4,647,447 A | 3/1987 | Gries et al. | |
| 4,702,998 A | 10/1987 | Tanaka et al. | |
| 4,749,560 A | 6/1988 | Elgavish | |
| 4,952,289 A | 8/1990 | Ciccone et al. | |
| 5,096,724 A | 3/1992 | Zenner et al. | |
| 5,162,109 A | 11/1992 | Rajagopalan et al. | |
| 5,322,681 A | 6/1994 | Klaveness | |
| 5,772,982 A * | 6/1998 | Coward | 424/1.73 |
| 5,874,421 A * | 2/1999 | Riley et al. | 514/161 |
| 6,084,093 A * | 7/2000 | Riley et al. | 540/465 |
| 6,204,259 B1* | 3/2001 | Riley et al. | 514/184 |
| 6,214,817 B1* | 4/2001 | Riley et al. | 514/186 |
| 6,525,041 B1* | 2/2003 | Neumann et al. | 514/184 |

FOREIGN PATENT DOCUMENTS

| | | |
|---|---|---|
| EP | 0281463 | 9/1988 |
| EP | 0287465 | 10/1988 |
| EP | 0296522 | 12/1988 |
| EP | 0374929 | 12/1989 |
| EP | 0391766 | 3/1990 |
| EP | 0457438 | 4/1991 |
| EP | 0524161 | 1/1993 |
| EP | 0588229 | 3/1994 |
| WO | WO 82/04252 | 12/1982 |
| WO | WO 89/11868 | 12/1989 |
| WO | WO 91/10645 | 7/1991 |
| WO | WO 92/08707 | 5/1992 |
| WO | WO 92/21017 | 11/1992 |
| WO | WO 93/05049 | 3/1993 |
| WO | WO 93/06868 | 4/1993 |
| WO | WO 93/12097 | 6/1993 |
| WO | WO 93/14093 | 7/1993 |
| WO | WO 94/15925 | 7/1994 |
| WO | WO 94/26315 | 11/1994 |
| WO | WO 95/10185 | * 4/1995 |
| WO | WO 95/28968 | 11/1995 |
| WO | WO 96/39396 | 12/1996 |
| WO | WO 96/40658 | 12/1996 |

OTHER PUBLICATIONS

Aston et al., "Asymmetric Synthesis of Highly Functionalized Polyaza Macrocycles via Reduction of Cyclic Peptide Precursors," Tetrahedron Letters, 1994, pp. 3687-3690, vol. 35.

(Continued)

Primary Examiner—Dameron L. Jones
(74) Attorney, Agent, or Firm—Sonnenschein Nath & Rosenthal LLP

(57) ABSTRACT

The present invention is directed to bioconjugates of complexes represented by the formula:

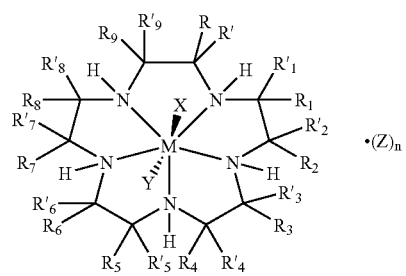

wherein R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, M, X, Y, Z and n are defined herein for use as contrast agents in diagnostic imaging.

5 Claims, No Drawings

OTHER PUBLICATIONS

Brady, "Practical Synthesis of Cyclic Peptides, with an Example of Dependence of Cyclization Yield upon Linear Sequence", J. Org. Chem., 1979, vol. 44 p. 3101.

Dizio et al., "Progestins-Rhenium Complexes: Metal-Labeled Steriods with High Receptor Binding Affinity, Potential Receptor-Directed Agents for Diagnostic Imaging or Therapy", Bioconjugate Chemistry, 1991, vol. 2, pp. 353-366.

Dizio et al., "Technetium-and Rhenium-Labeled Progestins: Synthesis, Receptor Binding and In Vivo Distribution of an 11β-Substituted Progestin Labeled with Technetium-99 and Rhenium-186", Journal of Neculear Medicine, vol. 33, No. 4, 1992, pp. 558-569.

Geraldes et al., "Magnetic Field Dependence of Solvent Proton Relaxation Rates Induced by $Gd^{3+}$ and $Mn^{2+}$ Complexes of Various Polyaza Macrocyclic Ligands: Implications for NMR Imaging," Magnetic Resonance in Medicine, pp. 242-250, vol. 3, 1986.

Hardy et al., "Superoxide Dismutase Mimetics Inhibit Neutrophil-Mediated Human Aortic Endothelial Cell Injury in Vitro," J. Biol. Chem., 1994, pp. 18535-18540, vol. 269.

Jackels et al., "Aqueous Proton NMR Relaxation Enhancement by Manganese (II) Macrocyclic Complexes: Structure Relaxivity Relationships," Inorganic Chemistry, 1992, pp. 234-239, vol. 31.

Jackels et al., "Paramagnetic Macrocyclic Complexes as Contrast Agents for MR Imaging: Proton Nuclear Relaxation Rate Enhancement in Aqueous Solution and in Rat Tissues," Radiology, 1992, pp. 27-31, vol. 3.

Lennon et al., "New Conformationally Constrained Polyaa Macrocycles Prepared via the Bis(chloroacetamide) Method," Tetrahedron Letters, 1994, pp. 853-856, vol. 35.

Maeda et al., "Antitumor Activity and Tissue Distribution of bis(bilato)-1,2," Database Chemabs (Chemical Abstracts Service & Cancer Lett.), 1993, pp. 57-64, vol. 70.

Newton et al., "Synthesis and Characterization of the Mn(II) Complex of [15]ane$N_5$," J. Coord. Chem., 1988, pp. 265-277, vol. 19.

Teijin Ltd., Patent Abstracts of Japan corresponding to JP-A-03 197 468, 1991, Abstract No. 461 (C-0887), vol. 15.

Szczpaniak, "Nuclear Magnetic Spin-Lattice Releaxation of Water Protons Caused by Metal Cage Compounds," Bioconjugate Chem., 1992, pp. 27-31, vol. 3.

Tosoh Corp., Patent Abstracts of Japan corresponding to JP-A-63 014 780, 1988, Abstract No. 219 (C-506), vol. 12.

Tsuchida et al., "Amphiphilic Porphinatoirons Having Steroid Groups and Their Oxygen-Adduct Formation in an Aqueous Medium," Bull Chem. Soc. Japan, 1990, pp. 2323-2327, vol. 63.

* cited by examiner

US 7,407,645 B2

BIOCONJUGATES OF METAL COMPLEXES OF NITROGEN-CONTAINING MACROCYCLIC LIGANDS

CROSS-REFERENCE TO RELATED APPLICATIONS

This application claims the benefit of prior U.S. divisional application filed Apr. 1, 2003, Ser. No. 10/405,044 now abandoned, which claims the benefit of prior U.S. application Ser. No. 08/698,631, filed Aug. 16, 1996 now abandoned, which claims the benefit of prior U.S. provisional application No. 60/002,394, filed Aug. 17, 1995.

BACKGROUND OF THE INVENTION

This invention relates to compounds effective as contrast agents in diagnostic imaging. In one aspect, this invention relates to magnetic resonance imaging (MRI) of human or non-human animal subjects using metal complexes of substituted nitrogen-containing fifteen-membered macrocyclic ligands which are conjugated to a targeting biomecule as contrast agents. In another aspect, this invention relates to manganese(II) complexes of substituted nitrogen-containing fifteen-membered macrocyclic ligands which are conjugated to a targeting biomolecule as MRI contrast agents.

X-rays have long been used to produce images of human and non-human animal tissue, e.g. the internal organs of a patient, the patient being positioned between a source of X-rays and a film sensitive to the rays. Where organs interfere with the passage of the rays, the film is less exposed and the resulting developed film is indicative of the state of the organ.

More recently, nuclear magnetic resonance (NMR) has been developed as an imaging technique, i.e. MRI. MRI avoids the harmful effects sometimes attending X-ray exposure. For improved imaging with X-rays, patients have been given enhancers prior to imaging, either orally or parenterally. After a predetermined time interval for distribution of the enhancer through the patient, the image is taken. To obtain a good image it is desirable that the time after the taking of enhancer be kept to a minimum. On the other hand there is a decrease in effectiveness with time, so desirably the decay should be relatively slow so as to provide a substantial time interval during which imaging can be done.

In the NMR imaging process, protons in the water of the body relax via two mechanisms. The respective relaxation times are referred to as $T_1$ and $T_2$. The rate at which the relaxation process occurs may be altered for some water molecules by giving values that contrast with the norm.

Compounds that enhance NMR images, referred to as contrast agents, are generally paramagnetic in nature. These may be organic free radicals or transition/lanthanide metals which have from one to seven unpaired electrons.

A necessary prerequisite of any ligand that binds a metal to form a contrast agent is that the resulting contrast agent be stable so as to prevent the loss of the metal and its subsequent accumulation in the body. Other considerations include an ability to reversibly bind water, which in turn increases it contrastability and decreases the dose level required. This ability is clearly important since the interaction between any two nuclear spins through space decreases at a rate equal to the reciprocal of the distance raised to the sixth power.

U.S. Pat. No. 4,647,447 discloses use of an NMR image enhancer consisting of the salt of an anion of a complexing acid and a paramagnetic metal anion. A preferred embodiment is the gadolinium chelate of diethylenetriaminepentaacetic acid (Gd DTPA), which is now commercially available from Nycomed Salutar, Inc. under the trade name Magnevist for use as an NMR contrast agent. From the data reported therein these appear to perform well. However, this compound is rapidly excreted by the kidneys, making the timing of the injection extremely critical. Furthermore, there is virtually no uptake by any solid-organ, such as the heart, pancreas or liver.

However, while a number of gadolinium contrast agents are known, there remains the possibility that small amounts of free lanthanides are being released, by decomposition of the agent, into the body. Not being a naturally existing metal in the body, little is known about long term effects.

Other nitrogen-containing macrocyclic ligands have been suggested for use as NMR contrast agents. Jackels, S. C. et al, "Aqueous Proton NMR Relaxation Enhancements by Manganese(II) Macrocyclic Complexes: Structure-Relaxivity Relationships", *Inorg. Chem.*, 31, 234-239 (1992) discloses fifteen-membered nitrogen-containing ring complexes. However, these compounds suffer from being insufficiently stable and/or colored, and as such are inadequate for application as MRI contrast agents.

Therefore, it would be highly desirable to develop alternative contrast agents which avoid one or more of the aforementioned disadvantages. It would also be desirable to be able to direct the contrast agents to a desired target in the body where the compound can be concentrated for optimal effect. Without some way to render the compounds "targeting", increased dosages are sometimes necessary in order to obtain an efficacious concentration at the site of interest. Such increased dosages can sometimes result in undesirable side effects in the patient.

It has now been discovered that metal complexes of substituted nitrogen-containing macrocyclic ligands which have increased kinetic, thermodynamic and oxidative stability, and which can be substituted to control lipophilicity, i.e. biodistribution, avoid the problems of the aforementioned contrast agents while providing good contrastability. It has also now been found that the macrocycles or metal complexes of the present invention can be attached, i.e. conjugated, to one or more targeting biomolecule(s) via a linker group to form a targeting biomolecule-macrocycle or targeting biomolecule-metal complex conjugate.

SUMMARY OF THE INVENTION

It is an object of the invention to provide magnetic resonance imaging (MRI) contrast agents having kinetic stability, i.e. the rate at which the paramagnetic metal dissociates from the metal complexes of the invention. It is a further object of the invention to provide bioconjugates of metal complexes of nitrogen-containing fifteen-membered macrocyclic ligands that are useful as MRI contrast agents in which the biodistribution of the contrast agents can be controlled. It is yet a further object of the invention to provide MRI contrast agents having oxidative stability and hydrogen bonding. It is a still further object of the invention to provide metal complexes which are useful as X-ray or ultrasound contrast agents, and which can be used in scintigraphy and radiotherapy.

According to the invention, bioconjugates of metal complexes of nitrogen-containing fifteen-membered macrocyclic ligands are provided wherein (1) one to five of the "R" groups are attached to biomolecules via a linker group. (2) one of X, Y and Z is attached to a biomolecule via a linker group, or (3) one to five of the "R" groups and one of X, Y and Z are attached to biomolecules via a linker group; and biomolecules are independently selected from the group consisting of steroids, carbohydrates, fatty acids, amino acids, peptides, proteins, antibodies, vitamins, lipids, phospholipids, phosphates, phosphonates, nucleic acids, enzyme substrates, enzyme inhibitors and enzyme receptor substrates and the linker group is derived from a substituent attached to the "R" group or X, Y and Z which is reactive with the biomolecule and is selected from the group consisting of —$NH_2$, —$NHR_{10}$, —SH, —OH, —COOH, —$COOR_{10}$, —$CONH_2$, —NCO, —NCS, —COOX", alkenyl, alkynyl, halide, tosylate, mesylate, tresylate, triflate and phenol, wherein $R_{10}$ is alkyl, aryl, or alkylaryl and X" is a halide.

Further according to the invention, a method of magnetic resonance imaging is provided which comprises administering to a human or non-human animal subject a contrast medium comprising a physiologically compatible paramagnetic metal complex of the present invention and a non-toxic, pharmaceutically acceptable carrier, adjuvant or vehicle, and generating a magnetic resonance image of at least a part of the subject.

Further according to the invention, a method of diagnostic imaging is provided which comprises administering to a human or non-human animal subject a diagnostic agent comprising a physiologically compatible heavy metal complex of the present invention and a non-toxic, pharmaceutically acceptable carrier, adjuvant or vehicle, and generating an X-ray, ultrasound or scintigraphic image of at least a part of the subject.

Further according to the invention, a method of radiotherapy practiced on a human or non-human animal subject is provided which comprises administering to the subject a radioactive agent comprising a physiologically compatible radioactive metal complex of the present invention and a non-toxic, pharmaceutically acceptable carrier, adjuvant or vehicle.

DETAILED DESCRIPTION OF THE INVENTION

The metal complexes of the invention used as MRI contrast agents, as diagnostic agents in X-ray, ultra-sound or scintigraphic image analysis, or as radiotherapy agents are represented by the formula:

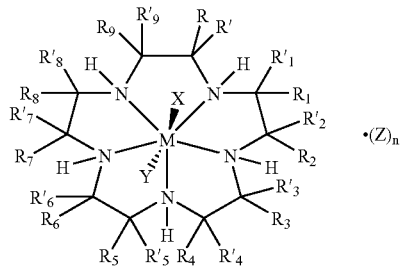

wherein R, R', $R_1$, $R_1'$, $R_2$, $R_2'$, $R_3$, $R_3'$, $R_4$, $R_4'$, $R_5$, $R_5'$, $R_6$, $R_6'$, $R_7$, $R_7'$, $R_8$, $R_8'$, $R_9$ and $R_9'$ independently represents hydrogen, alkyl, alkenyl, alkynyl, cycloalkyl, cycloalkenyl, cycloalkylalkyl, cycloalkylcycloalkyl, cycloalkenylalkyl, alkylcycloalkyl, alkenylcycloalkyl, alkylcycloalkenyl, alkenylcycloalkenyl, heterocyclic, aryl and aralkyl radicals and radicals attached to the α-carbon of α-amino acids; or $R_1$ or $R_1'$ and $R_2$ or $R_2'$, $R_3$ or $R_3'$ and $R_4$ or $R_4'$, $R_5$ or $R_5'$ and $R_6$ or $R_6'$, $R_7$ or $R_7'$ and $R_8$ or $R_8'$, and $R_9$ or $R_9'$ and R or R' together with the carbon atoms to which they are attached independently form a saturated, partially saturated or unsaturated cyclic having 3 to 20 carbon atoms; or R or R' and $R_1$ or $R_1'$, $R_2$ or $R_2'$ and $R_3$ or $R_3'$, $R_4$ or $R_4'$ and $R_5$ or $R_5'$, $R_6$ or $R_6'$ and $R_7$ or $R_7'$, and $R_8$ or $R_8'$ and $R_9$ or $R_9'$ together with the carbon atoms to which they are attached independently form a nitrogen containing heterocycle having 2 to 20 carbon atoms provided that when the nitrogen containing heterocycle is an aromatic heterocycle which does not contain a hydrogen attached to the nitrogen, the hydrogen attached to the nitrogen in said formula, which nitrogen is also in the macrocycle and the R groups attached to the same carbon atoms of the macrocycle are absent; and combinations thereof; and wherein (1) one to five of the "R" groups are attached to biomolecules via a linker group, (2) one of X, Y and Z is attached to a biomolecule via a linker group, or (3) one to five of the "R" groups and one of X, Y and Z are attached to biomolecules via a linker group; and biomolecules are independently selected from the group consisting of steroids, carbohydrates, fatty acids, amino acids, peptides, proteins, antibodies, vitamins, lipids, phospholipids, phosphates, phosphonates, nucleic acids, enzyme substrates, enzyme inhibitors and enzyme receptor substrates via a linker group wherein the linker group is derived from a substituent attached to the "R" group or X, Y and Z which is reactive with the biomolecule and is selected from the group consisting of —$NH_2$, —$NHR_{10}$, —SH, —OH, —COOH, —$COOR_{10}$, —$CONH_2$, —NCO, —NCS, —COOX", alkenyl, alkynyl, halide, tosylate, mesylate, tresylate, triflate and phenol, wherein $R_{10}$ is alkyl, aryl, or alkylaryl and X" is a halide.

X, Y and Z represent suitable ligands or charge-neutralizing anions which are derived from any monodentate or polydentate coordinating ligand or ligand system or the corresponding anion thereof (for example benzoic acid or benzoate anion, phenol or phenoxide anion, alcohol or alkoxide anion). X, Y and Z are independently selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyane, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid (such as acetic acid, trifluoroacetic acid, oxalic acid), aryl carboxylic acid (such as benzoic acid, phthalic acid), urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate aryl thiocarbamate, alkyl aryl thiocarbamate, alkyl dithiocarbamate, aryl dithiocarbamate, alkyl aryl dithiocarbamate, bicarbonate, carbonate, perchlorate, chlorate, chlorite, hypochlorite, perbromate, bromate, bromite, hypobromite, tetrahalomanganate, tetrafluoroborate, hexafluorophosphate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or systems where one or more of X, Y and Z are independently attached to one or more of the "R" groups, wherein n is an integer from 0 to 3. The preferred ligands from which X, Y and Z are selected include halide, organic acid, nitrate and bicarbonate anions.

The metal atoms or anions, M, which are suitable for use in the complexes of the invention as MRI contrast agents are paramagnetic metals having atomic numbers 21-29, 42-44 and 57-71. The complexes for use as MRI contrast agents are those wherein the preferred metal is Eu, Gd, Dy, Ho, Cr, Mn or Fe, more preferably Gd(III) or Mn(II), and most preferably Mn(II).

The metal atoms or anions, M, which are suitable for use in the complexes of the invention as X-ray or ultrasound contrast agents are heavy metals having atomic numbers 20-32, 42-44, 49 and 57-83. The complexes for use as X-ray or ultrasound contrast agents are those wherein the preferred metal is a non-radioactive metal having atomic numbers 42-44, 49 and 57-83, and most preferably Gd, Dy or Yb.

The metal atoms or anions, M, of the complexes of the invention which are suitable for use in scintigraphic and radiotherapy are radioactive metals of any conventional complexable radioactive metal isotope, preferably those having atomic numbers 20-32, 42-44, 49 and 57-83. In scintigraphy, the most preferred metals are $^{99m}$Tc or $^{111}$In. In radiotherapy, the most preferred metals are $^{153}$Sm, $^{67}$Cu or $^{90}$Y.

The linker groups, also termed herein "linker", are derived from the specified functional groups attached to the "R" groups or X, Y and Z, and function to link the biomolecule to the "R" groups or X, Y and Z. The functional groups are selected from the group consisting of —NH$_2$, —NHR$_{10}$, —SH, —OH, —COOH, —COOR$_{10}$, —CONH$_2$, —NCO, —NCS, —COOX", alkenyl, alkynyl, halide, tosylate, mesylate, tresylate, triflate and phenol wherein R$_{10}$ is alkyl, aryl, or alkaryl and X" is a halide. Currently, the preferred alkenyl group is ethenyl and the preferred alkynyl group is ethynyl. The functional groups on the "R" groups or X, Y and Z are reactive with the biomolecule, i.e. reactive with a functional group on the steroids, carbohydrates, fatty acids, amino acids, peptides, proteins, antibodies, vitamins, lipids, phospholipids, phosphates, phosphonates, nucleic acids, enzyme substrates, enzyme inhibitors, enzyme receptor substrates and other targeting biomolecules of interest. When the functional group attached to the "R" groups or X, Y and Z reacts with the biomolecule, the functional group is modified and it is this derived functional group which is the linker. For example, when an —NH$_2$ functional group attached to an "R" group is reacted with a steroid such as in Example 1, the linker is —NH—. The exact structure of specific linker groups will be readily apparent to those of ordinary skill in the art and will depend on the specific functional group and biomolecule selected. The specific reaction conditions for reacting a functional group attached to "R" groups or X, Y and Z with a biomolecule will be readily apparent to those of ordinary skill in the art.

The functional group useful to form the linker, defined herein as a "linker precursor", may be present on the "R" groups at the time the macrocycle is prepared or it may be added or modified after preparation of the macrocycle or metal complex thereof. Similarly, the linker precursor can be present on an axial ligand, i.e. X, Y or Z, when the metal complex is prepared or an exchange reaction of the axial ligands is conducted to exchange the axial ligands is conducted to exchange to axial ligand present in the metal complex.

The macrocycle of the present invention can be complexed with the metal either before or after conjugation with the targeting biomolecule depending on the specific biomolecule utilized. The conjugate of the macrocyclic complex and the targeting biomolecule is defined herein as a "bioconjugate".

Targeting of drugs is well known to those of ordinary skill in the art. See, for example, J. A. Katzenellenbogen et al, *Journal of Nuclear Medicine*, Vol. 33, No. 4, 1992, 558, and J. A. Katzenellenbogen et al, *Bioconjugate Chemistry*, 1991, 2, 353. Targeting agents are typically biomolecules. The biomolecules of the invention are biologically active molecules that are site specific, i.e. known to concentrate in the particular organ or tissue of interest. The biomolecules are selected to direct the tissue distribution of the bioconjugate via receptor binding, membrane association, membrane solubility, and the like. These biomolecules include, for example, steroids, carbonhydrates (including monosaccharides, disaccharides and polysaccharides), fatty acids, amino acids, peptides, proteins, antibodies (including polyclonal and monoclonal and fragments thereof), vitamins, lipids, phospholipids, phosphates, phosphonates, nucleic acids, enzyme substrates, enzyme inhibitors and enzyme receptor substrates. The biomolecules also include those biomolecules which are combinations of the above biomolecules, such as a combination of a steroid with a carbohydrate, e.g. digitonin.

The particular biomolecules which can be utilized to target a desired organ or tissue are known in the art or it will be readily apparent to those of ordinary skill in the art. The biomolecules of the invention are commercially available or can readily be prepared by one of ordinary skill in the art using conventional methods.

It is currently preferred that a maximum of one "R" group attached to the carbon atoms located between nitrogen atoms in the macrocycle has a biomolecule attached via a linker. In addition, the preferred compounds are those which have one to five, most preferably one to two, of the "R" groups attached to biomolecules and none of X, Y and Z attached to a biomolecule, or those which have one of X, Y and Z attached to a biomolecule and none of the "R" groups attached to a biomolecule.

Currently, the preferred compounds are those wherein at least one, more preferably at least two, of the "R" groups, in addition to the "R" groups which are attached to a biomolecule, represent alkyl, cycloalkyl, alkyl and aralkyl radicals and the remaining "R" groups not attached to a biomolecule represent hydrogen, a saturated, partially saturated or unsaturated cyclic or a nitrogen containing heterocycle. Other preferred groups of compounds are those wherein at least one, preferably two, of R$_1$ or R'$_1$ and R$_2$ or R'$_2$, R$_3$ or R'$_3$ and R$_4$ or R'$_4$, R$_5$ or R'$_5$ and R$_6$ or R'$_6$, R$_7$ or R'$_7$ and R$_8$ or R'$_8$, and R$_9$ or R'$_9$ and R or R' together with the carbon atoms to which they are attached represent a saturated, partially saturated or unsaturated cyclic having 3 to 20 carbon atoms and the remaining "R" groups in addition to the "R" groups which are attached to a biomolecule via a linker are hydrogen, nitrogen containing heterocycles or alkyl groups, and those wherein at least one, preferably two, of R or R' and R$_1$ or R'$_1$, R$_2$ or R'$_2$ and R$_3$ or R'$_3$, R$_4$ or R'$_4$ and R$_5$ or R'$_5$, R$_6$ or R'$_6$, and R$_7$ or R'$_7$, and R$_8$ or R'$_8$ and R$_9$ or R'$_9$ together with the carbon atoms to which they are attached are bound to form a nitrogen containing heterocycle having 2 to 20 carbon atoms and the remaining "R" groups in addition to the "R" groups which are attached to a biomolecule via a linker are independently selected from hydrogen, saturated, partially saturated or unsaturated cyclics or alkyl groups.

As used herein, "R" groups means all of the R groups attached to the carbon atoms of the macrocycle, i.e., R, R', R$_1$, R'$_1$, R$_2$, R'$_2$, R$_3$, R'$_3$, R$_4$, R'$_4$, R$_5$, R'$_5$, R$_6$, R'$_6$, R$_7$, R'$_7$, R$_8$, R'$_8$, R$_9$ and R'$_9$.

As utilized herein, the term "alkyl", alone or in combination, means a straight-chain or branched-chain alkyl radical containing from 1 to about 22 carbon atoms, preferably from about 1 to about 18 carbon atoms, and most preferably from about 1 to about 12 carbon atoms which optionally carries one or more substituents selected from (1) —NR$_{30}$R$_{31}$ wherein $R_{30}$ and $R_{31}$ are independently selected from hydrogen, alkyl, aryl or aralkyl; or $R_{30}$ is hydrogen, alkyl, aryl or aralkyl and $R_{31}$ is selected from the group consisting of —$NR_{32}R_{33}$, —OH, —$OR_{34}$,

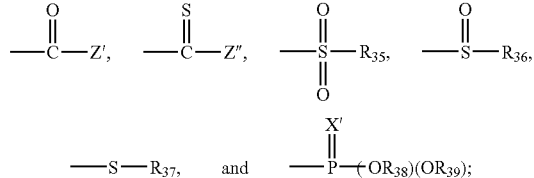

wherein $R_{32}$ and $R_{33}$ are independently hydrogen, alkyl, aryl or acyl, $R_{34}$ is alkyl, aryl or alkaryl, Z' is hydrogen, alkyl, aryl, alkaryl, —$OR_{34}$, —$SR_{34}$ or —$NR_{40}R_{41}$ wherein $R_{40}$ and $R_{41}$ are independently selected from hydrogen, alkyl, aryl or alkaryl, Z" is alkyl, aryl, alkaryl, —$OR_{34}$, —$SR_{34}$ or —$NR_{40}R_{41}$, $R_{35}$ is alkyl, aryl, —$OR_{34}$, or —$NR_{40}R_{41}$, $R_{36}$ is alkyl, aryl or —$NR_{40}R_{41}$, $R_{37}$ is alkyl, aryl or alkaryl, X' is oxygen or sulfur, and $R_{38}$ and $R_{39}$ are independently selected from hydrogen, alkyl or aryl;

(2) —$SR_{42}$ wherein $R_{42}$ is hydrogen, alkyl, aryl, alkaryl, —$SR_{34}$, —$NR_{32}R_{33}$,

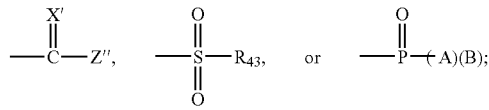

wherein $R_{43}$ is —OH, —$OR_{34}$ or —$NR_{32}R_{33}$, and A and B are independently —$OR_{34}$, —$SR_{34}$ or —$NR_{32}R_{33}$;

wherein x is 1 or 2, and $R_{44}$ is halide, alkyl, aryl, alkaryl, —OH, —$OR_{34}$, —$SR_{34}$ or —$NR_{32}R_{33}$;

(4) —$OR_{45}$ wherein $R_{45}$ is hydrogen, alkyl, aryl, alkaryl,

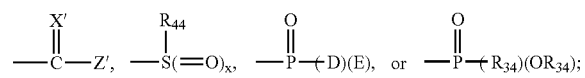

wherein D and E are independently —$OR_{34}$ or —$NR_{32}R_{33}$;

wherein $R_{46}$ is halide, —OH, —SH, —$OR_{34}$, —$SR_{34}$ or —$NR_{32}R_{33}$; or (6) amine oxides of the formula

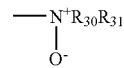

provided $R_{30}$ and $R_{31}$ are not hydrogen; or

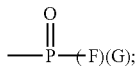

wherein F and G are independently —OH, —SH, —$OR_{34}$, —$SR_{34}$ or —$NR_{32}R_{33}$; or (8) —O—(—$(CH_2)_a$—O)$_b$—$R_{10}$ wherein $R_{10}$ is hydrogen or alkyl, and a and b an integers independently selected from 1+6; or (9) halogen, cyano, nitro, or azido. Alkyl, aryl and alkaryl groups on the substituents of the above-defined alkyl groups may contain one additional substituent but are preferably unsubstituted. Examples of such radicals include, but are not limited to, methyl, ethyl, n-propyl, isopropyl, n-butyl, isobutyl, sec-butyl, tert-butyl, pentyl, isoamyl, hexyl, octyl, nonyl, decyl, dodecyl, tetradecyl, hexadecyl, octadecyl and eicosyl. The term "alkenyl", alone or in combination, means an alkyl radical having one or more double bonds. Examples of such alkenyl radicals include, but are not limited to, ethenyl, propenyl, 1-butenyl, cis-2-butenyl, trans-2-butenyl, iso-butylenyl, cis-2-pentenyl, trans-2-pentenyl, 3-methyl-1-butenyl, 2,3-dimethyl-2-butenyl, 1-pentenyl, 1-hexenyl, 1-octenyl, decenyl, dodecenyl, tetradecenyl, hexadecenyl, cis- and trans-9-octadecenyl, 1,3-pentadienyl, 2,4-pentadienyl, 2,3-pentadienyl, 1,3-hexadienyl, 2,4-hexadienyl, 5,8,11,14-eicosatetraenyl, and 9,12,15-octadecatrienyl. The term "alkynyl", alone or in combination, means an alkyl radical having one or more triple bonds. Examples of such alkynyl groups include, but are not limited to, ethynyl, propynyl (propargyl), 1-butynyl, 1-octynyl, 9-octadecynyl, 1,3-pentadiynyl, 2,4-pentadiynyl, 1,3-hexadiynyl, and 2,4-hexadiynyl. The term "cycloalkyl", alone or in combination means a cycloalkyl radical containing from 3 to about 10, preferably from 3 to about 8, and most preferably from 3 to about 6, carbon atoms. Examples of such cycloalkyl radicals include, but are not limited to, cyclopropyl, cyclobutyl, cyclopentyl, cyclohexyl, cycloheptyl, cyclooctyl, and perhydronaphthyl. The term "cycloalkylalkyl" means an alkyl radical as defined above which is substituted by a cycloalkyl radical as defined above. Examples of cycloalkylalkyl radicals include, but are not limited to, cyclohexylmethyl, cyclopentylmethyl, (4-isopropylcyclohexyl)methyl, (4-t-butyl-cyclohexyl)methyl, 3-cyclohexylpropyl, 2-cyclo-hexylmethylpentyl, 3-cyclopentylmethylhexyl, 1-(4-neopentylcyclohexyl)methylhexyl, and 1-(4-isopropylcyclohexyl)methylheptyl. The term "cycloalkylcycloalkyl" means a cycloalkyl radical as defined above which is substituted by another cycloalkyl radical as defined above. Examples of cycloalkylcycloalkyl radicals include, but are not limited to, cyclohexylcyclopentyl and cyclohexylcyclohexyl. The term "cycloalkenyl", alone or in combination, means a cycloalkyl radical having one or more double bonds. Examples of cycloalkenyl radicals include, but are not limited to, cyclopentenyl, cyclohexenyl, cyclooctenyl, cyclopentadienyl, cyclohexadienyl and cyclooctadienyl. The term "cycloalkenylalkyl" means an alkyl radical as defined above which is substituted by a cycloalkenyl radical as defined above. Examples of cycloalkenylalkyl radicals include, but are not limited to, 2-cyclohexen-1-ylmethyl, 1-cyclopenten-1-ylmethyl, 2-(1-cyclohexen-1-yl)ethyl, 3-(1-cyclopenten-1-yl)propyl, 1-(1-cyclohexen-1-ylmethyl)pentyl, 1-(1-cyclopenten-1-yl)hexyl, 6-(1-cyclohexen-1-yl)hexyl, 1-(1-cyclopenten-1-yl)nonyl and 1-(1-cyclohexen-1-yl)nonyl. The terms "alkylcycloalkyl" and "alkenylcycloalkyl" mean a cycloalkyl radical as defined above which is substituted by an alkyl or alkenyl radical as defined above. Examples of alkylcycloalkyl and alkenylcycloalkyl radicals include, but are not limited to, 2-ethylcyclobutyl, 1-methylcyclopentyl, 1-hexylcyclopentyl, 1-methylcyclohexyl, 1-(9-octadecenyl)cyclopentyl and 1-(9-octadecenyl)cyclohexyl. The terms "alkylcycloalkenyl" and "alkenylcycloalkenyl" means a cycloalkenyl radical as defined above which is substituted by an alkyl or alkenyl radical as defined above. Examples of alkylcycloalkenyl and alkenylcycloalkenyl radicals include, but are not limited to, 1-methyl-2-cyclopentenyl, 1-hexyl-2-cyclopentenyl, 1-ethyl-2-cyclohexenyl, 1-butyl-2-cyclohexenyl, 1-(9-octadecenyl)-2-cyclohexenyl and 1-(2-pentenyl)-2-cyclohexenyl. The term "aryl", alone or in combination, means a phenyl or naphthyl radical which optionally carries one or more substituents selected from alkyl, cycloalkyl, cycloalkenyl, aryl, heterocycle, alkoxyaryl, alkaryl, alkoxy, halogen, hydroxy, amine, cyano, nitro, alkylthio, phenoxy, ether, trifluoromethyl and the like, such as phenyl, p-tolyl, 4-methoxyphenyl, 4-(tert-butoxy)phenyl, 4-fluorophenyl, 4-chlorophenyl, 4-hydroxyphenyl, 1-naphthyl, 2-naphthyl, and the like. The term "aralkyl", alone or in combination, means an alkyl or cycloalkyl radical as defined above in which one hydrogen atom is replaced by an aryl radical as defined above, such as benzyl, 2-phenylethyl, and the like. The term "heterocyclic" means ring structures containing at least one other kind of atom, in addition to carbon, in the ring. The most common of the other kinds of atoms include nitrogen, oxygen and sulfur. Examples of heterocyclics include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups. The term "saturated, partially saturated or unsaturated cyclic" means fused ring structures in which 2 carbons of the ring are also part of the fifteen-membered macrocyclic ligand. The ring structure can contain 3 to 20 carbon atoms, preferably 5 to 10 carbon atoms, and can also contain one or more other kinds of atoms in addition to carbon. The most common of the other kinds of atoms include nitrogen, oxygen and sulfur. The ring structure can also contain more than one ring. The term "saturated, partially saturated or unsaturated ring structure" means a ring structure in which one carbon of the ring is also part of the fifteen-membered macrocyclic ligand. The ring structure can contain 3 to 20, preferably 5 to 10, carbon atoms and can also contain nitrogen, oxygen and/or sulfur atoms. The term "nitrogen containing heterocycle" means ring structures in which 2 carbons and a nitrogen of the ring are also part of the fifteen-membered macrocyclic ligand. The ring structure can contain 2 to 20, preferably 4 to 10, carbon atoms, can be partially or fully unsaturated or saturated and can also contain nitrogen, oxygen and/or sulfur atoms in the portion of the ring which is not also part of the fifteen-membered macrocyclic ligand. The term "organic acid anion" refers to carboxylic acid anions having from about 1 to about 18 carbon atoms. The term "halide" means chloride or bromide.

The overall charge-type of the complex can be varied from negative to positive by carbon substitution of the appropriate charged groups on the macrocyclic framework. While the manganese (II) complexes of the invention exist as monocations in methanol solution, the axial anions are labile and in vivo can rapidly exchange with endogenous charged or uncharged ligands. By considering the dipositive nature of the manganese (II) metal center, the overall charge on the complex can be adjusted as needed to enhance desired pharmaceutical properties such as osmolality, tissue distribution and non-target clearance. For example, if the complex carries only charge neutral functionality, such as C-alkyl substitution, then the overall charge on the complex will be determined by the manganese center and will be positive. Multi-positive complexes are available via the incorporation of pendant cations such as protonated aminoalkyl groups. These types of complexes can bind to endogenous anions, anionic proteins, cell membranes, and the like. If two pendant anionic groups are attached, such as two carboxylates, phenolate, phosphonates, sulfonates and the like, the overall charge on the complex can be envisioned as zero. Alternatively, if three or more pendant anionic groups are attached, then an anionic complex will result. The pendant groups may be designed to axially chelate and formally displace the axial anions or they may be designed specifically to not chelate but retain a charge type.

The substituents on the complex of the invention, i.e. the "R" groups other than hydrogen and those attached to biomolecules via a linker group, are those groups which result in complexes having improved stability, controlled lipophilicity, improved hydrogen bonding and greater rigidity of the macrocyclic ligand.

Regarding rigidity of the macrocycle, groups which rigidify the macrocycle typically result in improved stability and improved inner- and outer-sphere relaxation. Examples of groups which improve rigidity of the macrocycle include, but are not limited to, cycloalkyl groups e.g. trans-cyclohexano, and multiple alkyl or substituted alkyl groups.

Regarding hydrogen bonding, groups that improve hydrogen bonding result in improved residence time of water to the metal complex by providing alternate binding sites. Examples of groups that improve hydrogen bonding include, but are not limited to, hydroxy alkyl or amino alkyl, e.g. hydroxymethyl or aminopropyl.

By varying the type and number of substituents, e.g. "R" groups which are other than hydrogen, the lipophilicity of the complexes can be controlled, i.e. the biodistribution of the complexes of the invention can be controlled, by preparing compounds which vary from hydrophilic to lipophilic. Therefore, the complexes of the invention can be targeted to various tissues or organs in the body by controlling the type and number of substitutents.

Kinetic stability of the metal complex is important because complexes which are not sufficiently kinetically stable dissociate and release free metal in the body. The kinetic stability, $k_{diss}$ ($M^{-1}sec^{-1}$), can be controlled by varying the type and number of substitutents which are other than hydrogen. Oxidative stability of the metal complex is a particular problem for Mn complexes and is important because complexes which are not sufficiently oxidatively stable will go from Mn(II) to Mn(III). Since the Mn(III) complexes are colored, it is necessary to maintain the complexes in the Mn(II) form to have a suitable contrast agent. By varying the type and number of substitutents, the oxidative stability, $E_{1/2}(v)$, is controlled. It is generally desired to select the type and number of substitutents such that $E_{1/2}$ is greater than about 0.7 v.

A first embodiment of the invention relates to a method of magnetic resonance imaging comprising (a) administering to a human or non-human animal subject a contrast medium comprising a physiologically compatible complex of the invention and a nontoxic pharmaceutically acceptable carrier, adjuvant or vehicle; and (b) generating a magnetic resonance image of at least a part of the human or non-human animal subject.

A second embodiment of the invention relates to a method of diagnostic imaging comprising (a) administering to a human or non-human animal subject a diagnostic agent comprising a physiologically compatible complex of the present invention and a nontoxic, pharmaceutically acceptable carrier, adjuvant or vehicle, and (b) generating an X-ray, ultrasound or scintigraphic image of at least a part of the human or non-human animal subject.

A third embodiment of the invention relates to a method of radiotherapy practiced on a human or non-human animal subject comprising administering to the human or non-human animal subject a radioactive agent comprising a physiologically compatible complex of the present invention wherein M is a radioactive metal, and a nontoxic, pharmaceutically acceptable carrier, adjuvant or vehicle.

A fourth embodiment of the invention relates to bioconjugates of metal complexes of nitrogen-containing fifteen-membered macrocyclic ligands of the present invention wherein the metal is selected from metals having atomic numbers 21-24, 26-29, 42-44, 49 or 57-83.

The macrocyclic ligands useful in the complexes of the present invention can be prepared according to the general procedure shown in Scheme A set forth below. Thus, an amino acid amide, which is the corresponding amide derivative of a naturally or non-naturally occurring α-amino acid, is reduced to form the corresponding substituted ethylenediamine. Such amino acid amide can be the amide derivative of any one of many well known amino acids. Preferred amino acid amides are those represented by the formula:

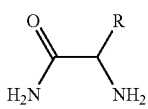

wherein R is derived from the D or L forms of the amino acids Alanine, Aspartic acid, Arginine, Asparagine, cysteine, Glycine, Glutamic acid, Glutamine, Histidine, Isoleucine, Leucine, Lysine, Methionine, Proline, Phenylalanine, Serine, Tryptophan, Threonine, Tyrosine, Valine and/or the R groups of unnatural α-amino acids such as alkyl, ethyl, butyl, tert-butyl, cycloalkyl, phenyl, alkenyl, allyl, alkynyl, aryl, heteroaryl, polycycloalkyl, polycycloaryl, polycycloheteroaryl, imines, aminoalkyl, hydroxyalkyl, hydroxyl, phenol, amine oxides, thioalkyl, carboalkoxyalkyl, carboxylic acids and their derivatives, keto, ether, aldehyde, amine, nitrile, halo, thiol, sulfoxide, sulfone, sulfonic acid, sulfide, disulfide, phosphonic acid, phosphinic acid, phosphine oxides, sulfonamides, amides, amino acids, peptides, proteins, carbohydrates, nucleic acids, fatty acids, lipids, nitro, hydroxylamines, hydroxamic acids, thiocarbonyls, borates, boranes, boraza, silyl, siloxy, silaza, and combinations thereof. Most preferred are those wherein R represents hydrogen, alkyl, cycloalkylalkyl, and aralkyl radicals. The diamine is then tosylated to produce the di-N-tosyl derivative which is reacted with a di-O-tosylated tris-N-tosylated triazaalkane diol to produce the corresponding substituted N-pentatosyl-pentaazacycloalkane. The tosyl groups are then removed and the resulting compound is reacted with a metal compound, e.g. a manganese(II) compound, under essentially anhydrous and anaerobic conditions to form the corresponding substituted metal, e.g. manganese(II), pentaazacycloalkane complex. When the ligands or charge-neutralizing anions, i.e. X, Y and Z, are anions or ligands that cannot be introduced directly from the metal, e.g. manganese, compound, the complex with those anions or ligands can be formed by conducting an exchange reaction with a complex that has been prepared by reacting the macrocycle with a metal, e.g. manganese, compound.

The complexes of the present invention, wherein $R_9$, and $R_2$ are alkyl, and $R_3$, $R'_3$, $R_4$, $R'_4$, $R_5$, $R'_5$, $R_6$, $R'_6$, $R_7$, $R'_7$, $R_8$ and $R'_8$ can be alkyl, arylalkyl or cycloalkylalkyl and R or R' and $R_1$ or $R'_1$ together with the carbon atoms they are attached to are bound to form a nitrogen containing heterocycle, can also be prepared according to the general procedure shown in Scheme B set forth below utilizing methods known in the art for preparing the metal, e.g. manganese(II), pentaazabicyclo[12.3.1]octadecapentaene complex precursor. See, for example, Alexander et al., Inorg. Nucl. Chem. Lett., 6, 445 (1970). Thus a 2,6-diketopyridine is condensed with triethylene tetraamine in the presence of a metal, e.g. manganese(II), compound to produce the metal, e.g. manganese(II), pentaazabicyclo[12.3.1]octadecapentaene complex. The metal, e.g. manganese(II), pentaazabicyclo[12.3.1]octadecapentaene complex is hydrogenated with platinum oxide at a pressure of 10-1000 psi to give the corresponding metal, e.g. manganese(II), pentaazabicyclo[12.3.1]octadecatriene complex.

The macrocyclic ligands useful in the complexes of the present invention can also be prepared by the diacid dichloride route shown in Scheme C set forth below. Thus, a triazaalkane is tosylated in a suitable solvent system to produce the corresponding tris (N-tosyl) derivative. Such a derivative is treated with a suitable base to produce the corresponding disulfonamide anion. The disulfonamide anion is dialkylated with a suitable electrophile to produce a derivative of a dicarboxylic acid. This derivative of a dicarboxylic acid is treated to produce the dicarboxylic acid, which is then treated with a suitable reagent to form the diacid dichloride. The desired vicinal diamine is obtained in any of several ways. One way which is useful is the preparation from an aldehyde by reaction with cyanide in the presence of ammonium chloride followed by treatment with acid to produce the alpha ammonium nitrile. The latter compound is reduced in the presence of acid and then treated with a suitable base to produce the vicinal diamine. Condensation of the diacid dichloride with the vicinal diamine in the presence of a suitable base forms the tris(tosyl)diamide macrocycle. The tosyl groups are removed and the amides are reduced and the resulting compound is reacted with a metal, e.g. manganese (II), compound under essentially anhydrous and anaerobic conditions to form the corresponding substituted pentaazacycloalkane metal, e.g. manganese (II), complex.

The vicinal diamines have been prepared by the route shown (known as the Strecker synthesis) and vicinal diamines were purchased when commercially available. Any method of vicinal diamine preparation could be used.

The macrocyclic ligands useful in the complexes of the present invention can also be prepared by the pyridine diamide route shown in Scheme D as set forth below. Thus, a polyamine, such as a tetraaza compound, containing two primary amines is condensed with dimethyl 2,6-pyridine dicarboxylate by heating in an appropriate solvent, e.g., methanol, to produce a macrocycle incorporating the pyridine ring as the 2,6-dicarboxamide. The pyridine ring in the macrocycle is reduced to the corresponding piperidine ring in the macrocycle, and then the diamides are reduced and the resulting compound is reacted with a metal, e.g. manganese (II), compound under essentially anhydrous and anaerobic conditions to form the corresponding substituted pentaazacycloalkane metal, e.g. manganese (II), complex.

The macrocyclic ligands useful in the complexes of the present invention can also be prepared by the bis(haloacetamide) route shown in Scheme E set forth below. Thus a triazaalkane is tosylated in a suitable solvent system to produce the corresponding tris (N-tosyl) derivative. Such a derivative is treated with a suitable base to produce the corresponding disulfonamide anion. A bis(haloacetamide), e.g., a bis(chloroacetamide), of a vicinal diamine is prepared by reaction of the diamine with an excess of haloacetyl halide, e.g., chloroacetyl chloride, in the presence of a base. The disulfonamide anion of the tris(N-tosyl)triazaalkane is then reacted with the bis(chloroacetamide) of the diamine to produce the substituted tris(N-tosyl, diamide macrocycle. The tosyl groups are removed and the amides are reduced and the resulting compound is reacted with a metal, e.g. manganese (II), compound under essentially anhydrous and anaerobic conditions to form the corresponding substituted pentaazacycloalkane metal, e.g. manganese (II), complex.

The macrocyclic ligands useful in the complexes of the present invention, wherein $R_1$, $R'_1$, $R_2$, $R'_2$ are derived from a diamino starting material and $R_5$, $R'_5$, $R_7$, $R'_7$ and $R_9$, $R'_9$ can be H or any functionality previously described, can be prepared according to the pseudo-peptide method shown in Scheme F set forth below. A substituted 1,2-diaminoethane represented by the formula

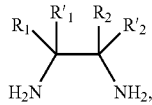

wherein $R_1$, $R'_1$, $R_2$ and $R'_2$ are the substituents on adjacent carbon atoms in the product macrocyclic ligand as set forth above, can be used in this method in combination with any amino acids. The diamine can be produced by any conventional method known to those skilled in the art. The R groups in the macrocycle derived from substituents on the α-carbon of α-amino acids, i.e. $R_5$, $R'_5$, $R_7$, $R'_7$, $R_9$ and $R'_9$, could be derived from the D or L forms of the amino acids Alanine, Aspartic acid, Arginine, Asparagine, Cysteine, Glycine, Glutamic acid, Glutamine, Histidine, Isoleucine, Leucine, Lysine, Methionine, Proline, Phenylalanine, Serine, Tryptophan, Threonine, Tyrosine, Valine and/or the R groups of unnatural α-amino acids such as alkyl, ethyl, butyl, tert-butyl, cycloalkyl, phenyl, alkenyl, allyl, alkynyl, aryl, heteroaryl, polycycloalkyl, polycycloaryl, polycycloheteroaryl, imines, aminoalkyl, hydroxyalkyl, hydroxyl, phenol, amine oxides, thioalkyl, carboalkoxyalkyl, carboxylic acids and their derivatives, keto, ether, aldehyde, amine, nitrile, halo, thiol, sulfoxide, sulfone, sulfonic acid, sulfide, disulfide, phosphonic acid, phosphinic acid, phosphine oxides, sulfonamides, amides, amino acids, peptides, proteins, carbohydrates, nucleic acids, fatty acids, lipids, nitro, hydroxylamines, hydroxamic acids, thiocarbonyls, borates, boranes, boraza, silyl, siloxy, silaza, and combinations thereof. As an example 1,8-dihydroxy, 4,5-diaminooctane is monotosylated and reacted with Boc anhydride to afford the differentiated N-Boc, N-tosyl derivative. The sulfonamide was alkylated with methyl bromoacetate using sodium hydride as the base and saponified to the free acid. The diamine containing N-tosylglycine serves as a dipeptide surrogate in standard solution-phase peptide synthesis. Thus, coupling with a functionalized amino acid ester affords the corresponding pseudo-tripeptide. Two sequential TFA cleavage-couplings affords the pseudo-pentapeptide which can be N- and C-terminus deprotected in one step using HCl/AcOH. DPPA mediated cyclization followed by LiAlH$_4$ or Borane reduction affords the corresponding macrocylic ligand. This ligand system is reacted with a metal, e.g. manganese (II), compound, such as manganese (II) chloride under essentially anaerobic conditions to form the corresponding functionalized manganese (II) pentaazacycloalkane complex. When the ligands or charge-neutralizing anions, i.e. X, Y and Z, are anions or ligands that cannot be introduced directly from the metal, e.g. manganese, compound, the complex with those anions or ligands can be formed by conducting an exchange reaction with a complex that has been prepared by reacting the macrocycle with a metal, e.g. manganese, compound.

The macrocyclic ligands useful in the complexes of the present invention, wherein $R_1$, $R'_1$, $R_3$, $R'_3$, $R_5$, $R'_5$, $R_7$, $R'_7$, $R_9$ and $R'_9$ can be H or any functionality as previously described, can be prepared according to the general peptide method shown in Scheme G set forth below. The R groups in the macrocycle derived from substitutents on the α-carbon of α-amino acids, i.e. $R_1$, $R'_1$, $R_3$, $R'_3$, $R_5$, $R'_5$, $R_7$, $R'_7$, $R_9$ and $R'_9$, are defined above in Scheme F. The procedure for preparing the cyclic peptide precursors from the corresponding linear peptides are the same or significant modifications of methods known in the art. See, for example, Veber, D. F. et al., J. Org. Chem., 44, 3101 (1979). The general method outlined in Scheme G below is an example utilizing the sequential solution-phase preparation of the functionalized linear pentapeptide from N-terminus to C-terminus. Alternatively, the reaction sequence to prepare the linear pentapeptide can be carried out by solid-phase preparation utilizing methods known in the art. The reaction sequence could be conducted from C-terminus to N-terminus and by convergent approaches such as the coupling of di- and tri-peptides as needed. Thus a Boc-protected amino acid is coupled with an amino acid ester using standard peptide coupling reagents. The new Boc-dipeptide ester is then saponified to the free acid which is coupled again to another amino acid ester. The resulting Boc-tri-peptide ester is again saponified and this method is continued until the Boc-protected pentapeptide free acid has been prepared. The Boc protecting group is removed under standard conditions and the resulting pentapeptide or salt thereof is converted to the cyclic pentapeptide. The cyclic pentapeptide is then reduced to the pentaazacyclopentadecane with lithium aluminum hydride or borane. The final ligand is then reacted with a metal, e.g. manganese, compound under essentially anaerobic conditions to form the corresponding metal, e.g. manganese, pentaazacyclopentadecane complex. When the ligands or charge-neutralizing anions, e.g. X, Y and Z, are anions or ligands that cannot be introduced directly from the metal, e.g. manganese, compound, the complex with those anions or ligands can be formed by conducting an exchange reaction with a complex that has been prepared by reacting the macrocycle with a metal, e.g. manganese, compound.

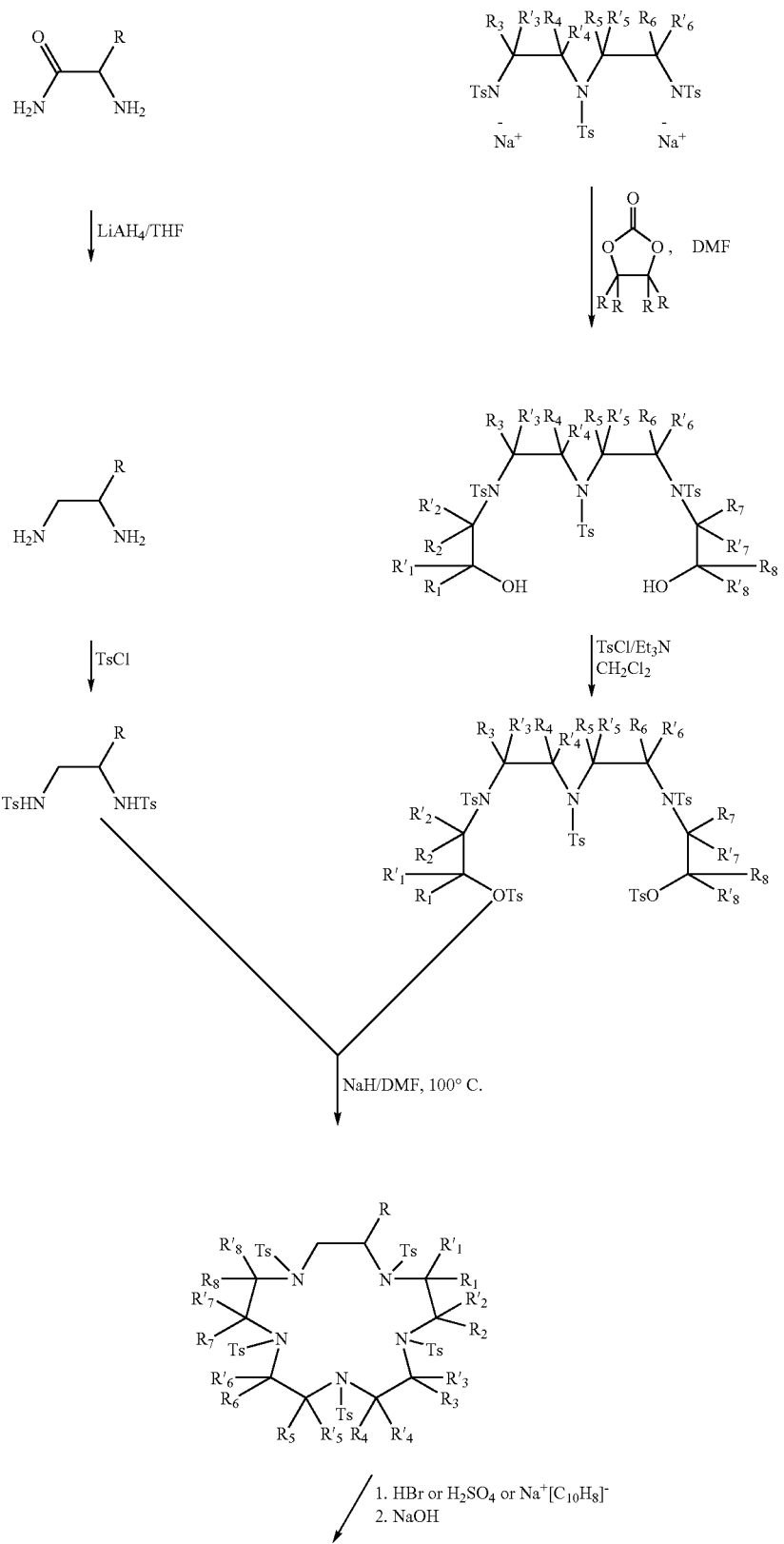

-continued
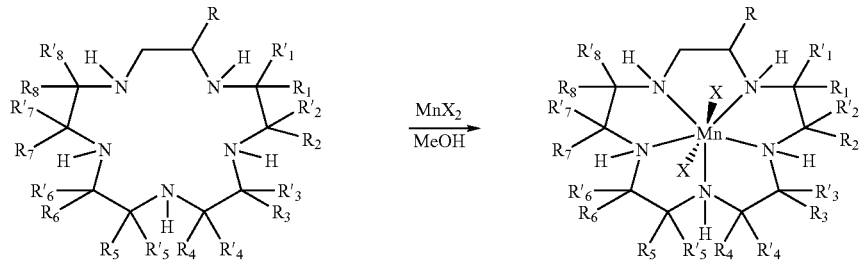
SCHEME B
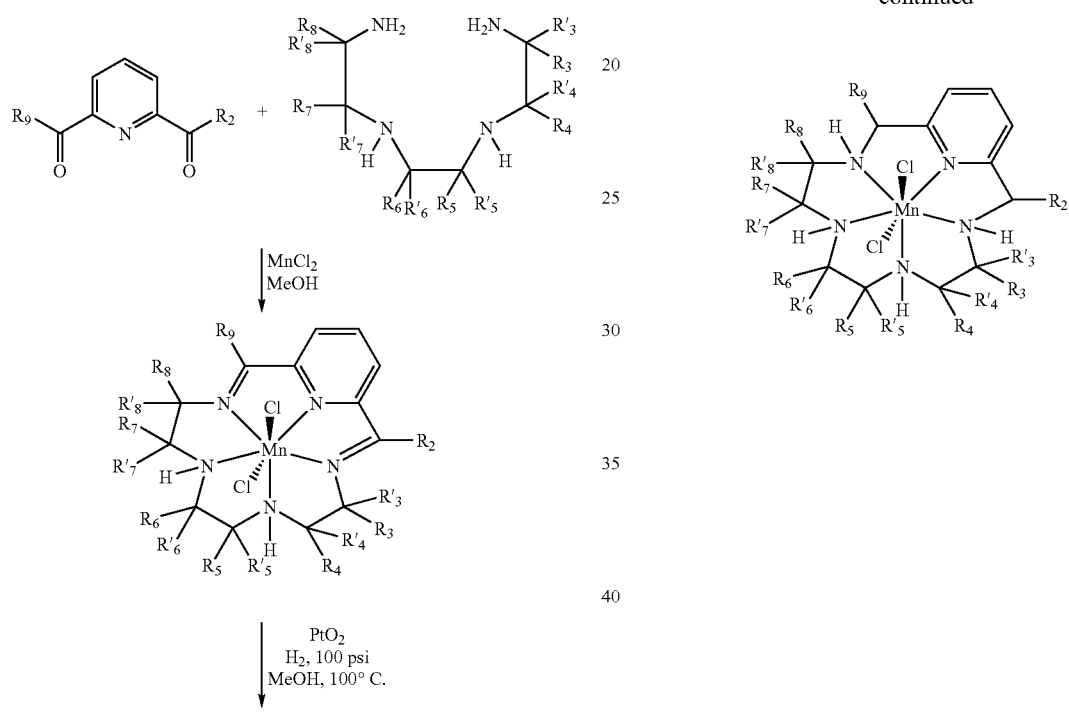
SCHEME C
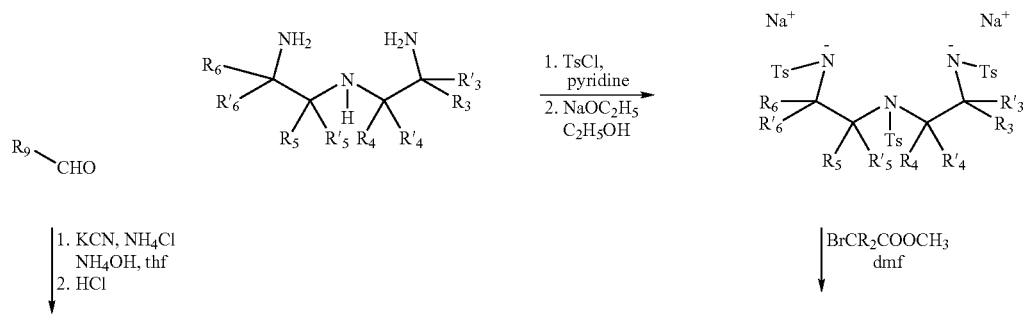

-continued
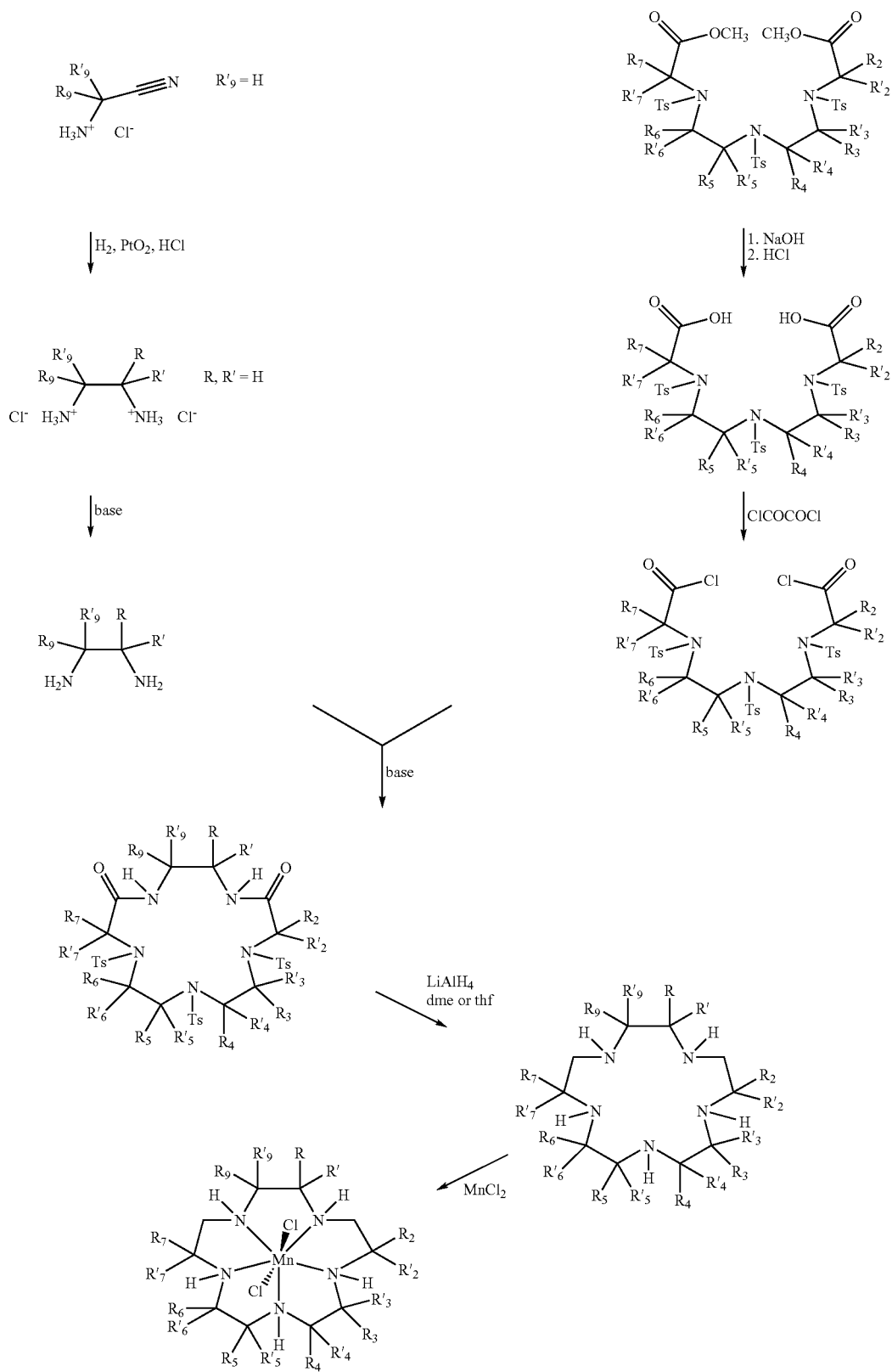

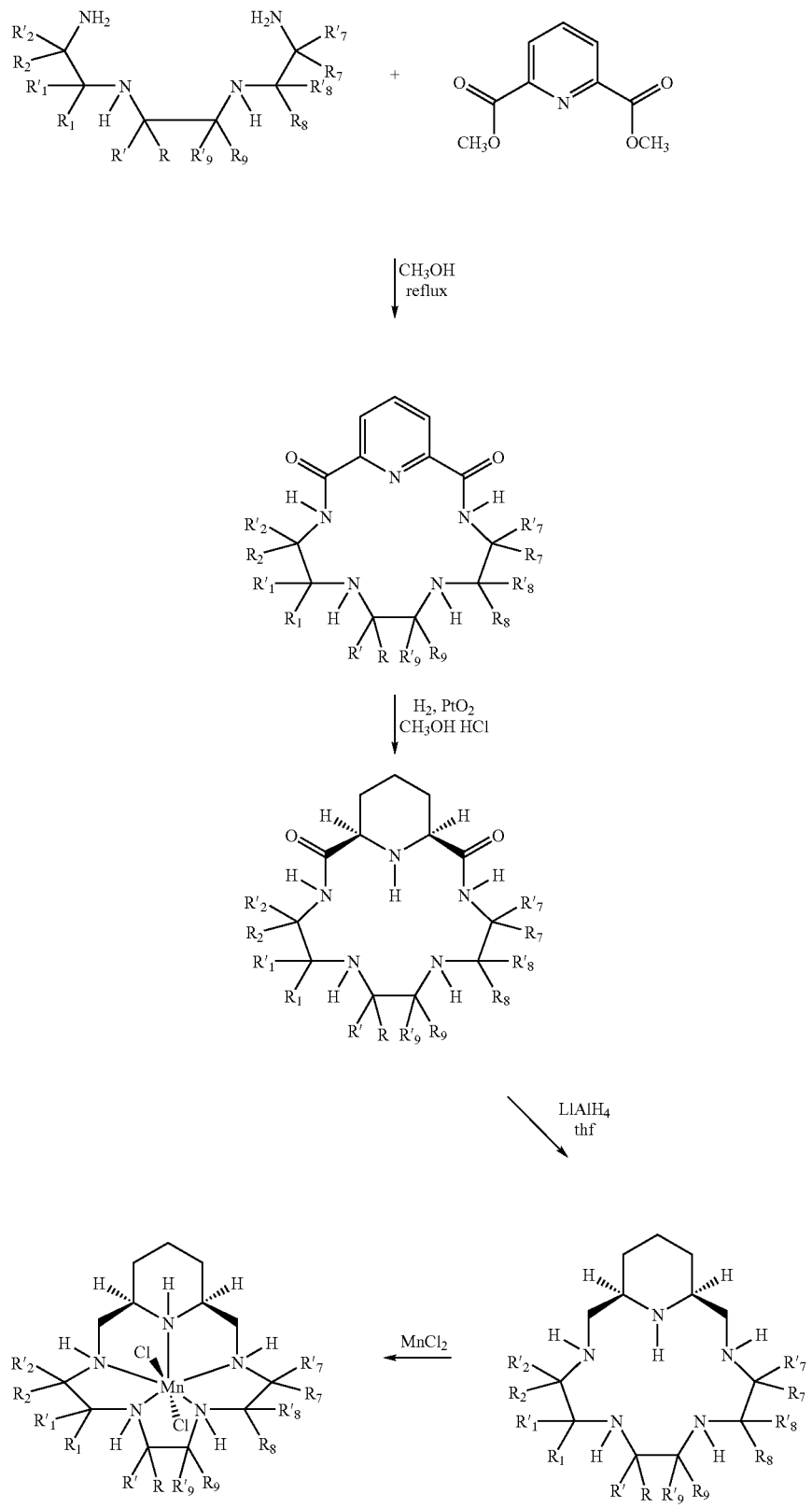

Scheme E
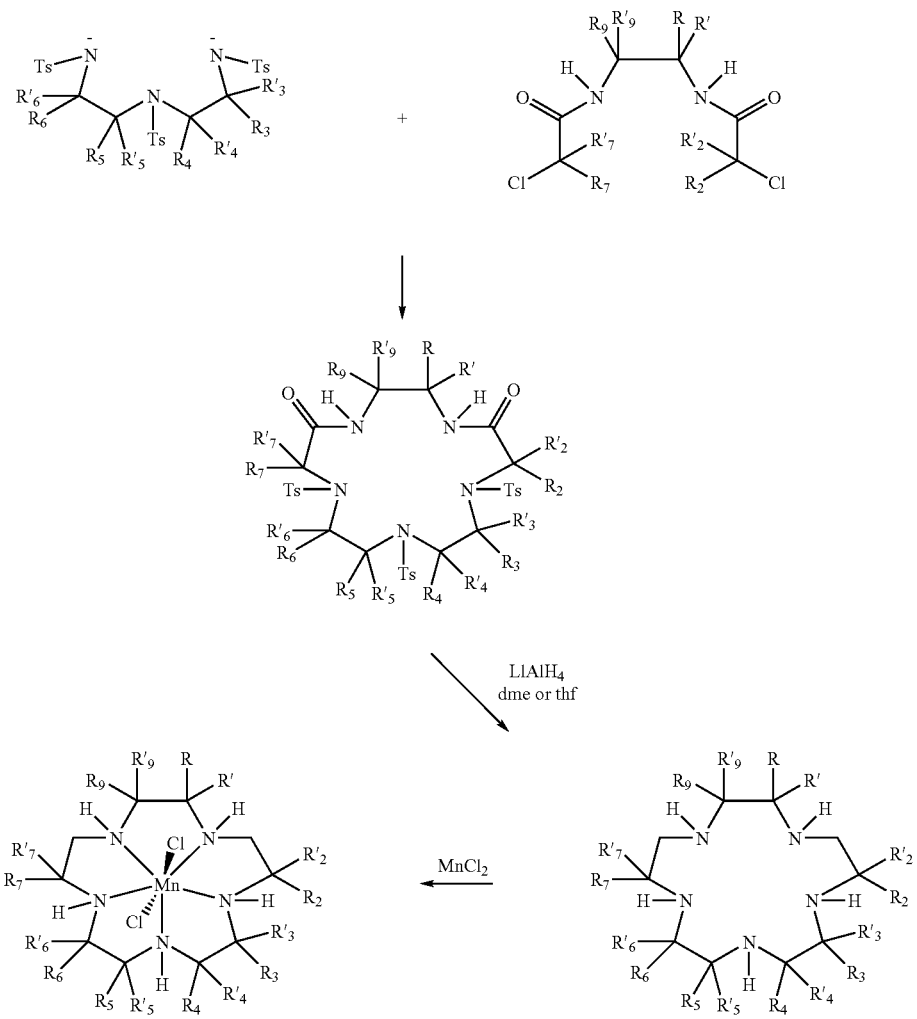
SCHEME F
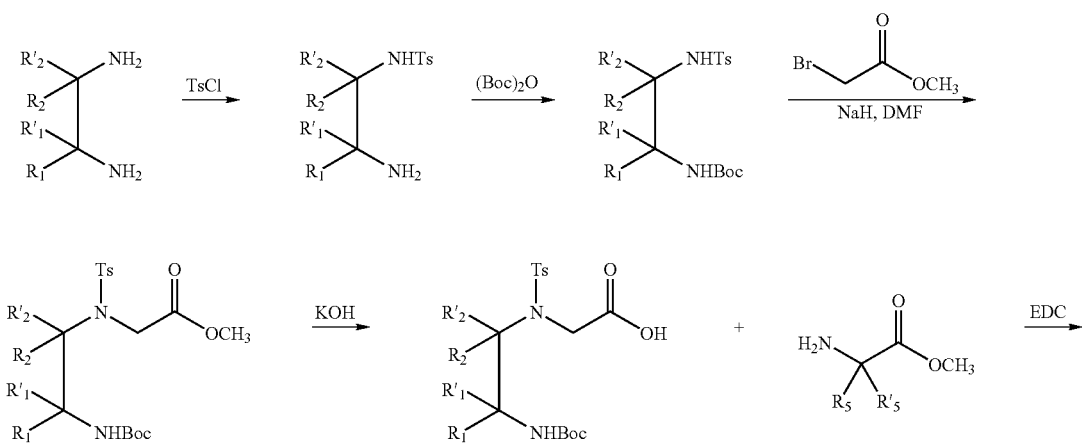

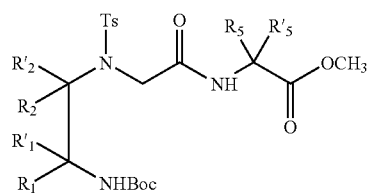
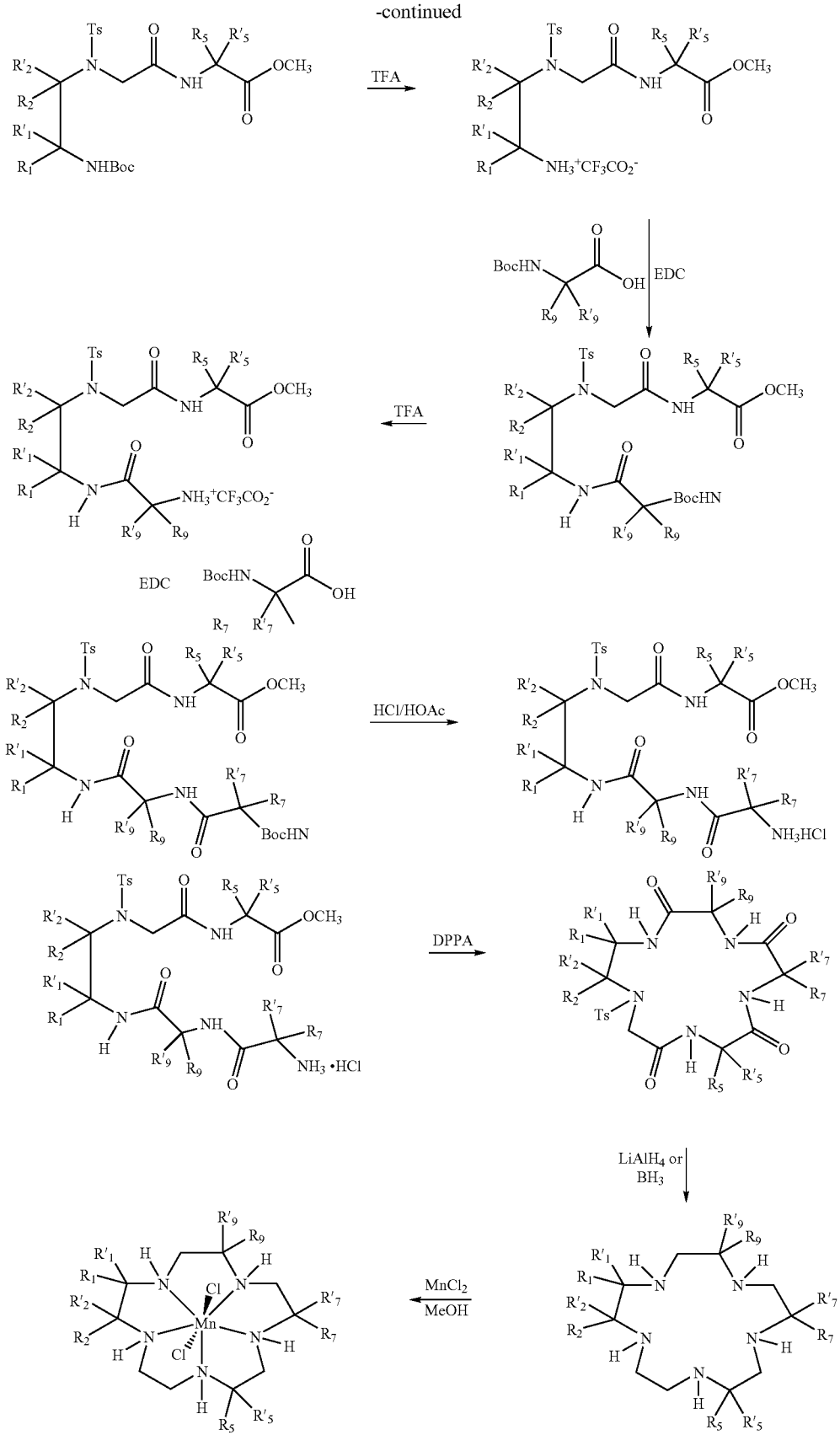

SCHEME G
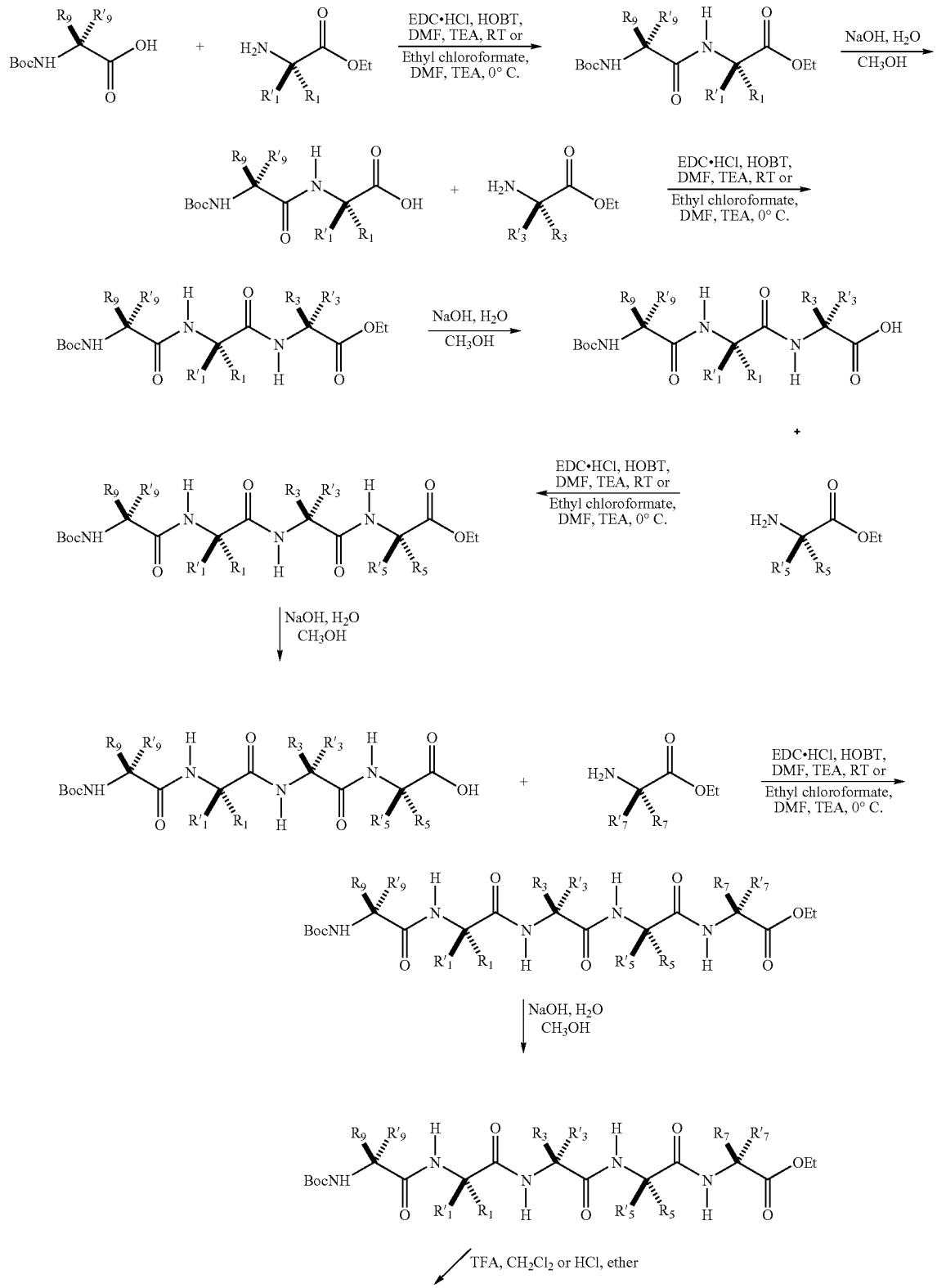

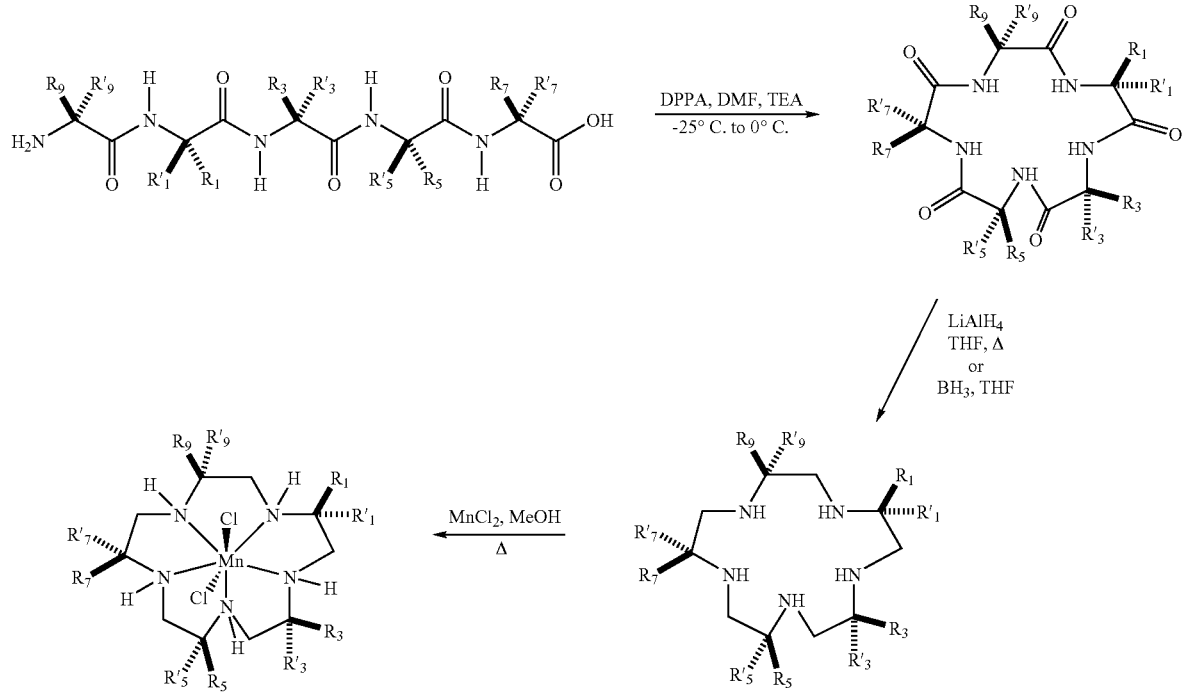

The pentaazamacrocycles of the present invention can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting one or more secondary amine group(s) of the compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure ligand. The optically active compounds of the invention can likewise be obtained by utilizing optically active starting materials, such as natural amino acids.

The methods of diagnostic analysis of the present invention involve administering the complexes, i.e. contrast enhancing agents, of the invention to a human or non-human animal subject or host, in an amount sufficient to effect the desired contrast (or shift) and then subjecting the host to diagnostic analysis. Preferably diagnostic analysis is NMR analysis; including and especially preferred, NMR imaging analysis (or MRI). Further, the complexes of the present invention are useful in diagnostic analysis by X-ray image analysis, ultrasonic analysis or scintigraphic analysis. While described primarily as contrast enhancing agents, the complexes of the invention can act as NMR shift reagents and such use is contemplated by the methods herein.

The complexes of the invention used as contrast enhancing agents are administered in an amount sufficient to effect the desired contrast. For NMR, this amount is an NMR signal effecting amount of the complex, i.e. any amount of said complex that will alter the spin-lattice, spin-spin or spin-echo relaxation times of an NMR signal or for a shift reagent, selectively shift the spectrical position of a resonance nucleus relative to other similar nuclei. This alteration is effected in a manner in order to enhance the signals received from the subject under analysis either by reducing the aforementioned relaxation times or by increasing them with respect to an area of the host or the host per se which has had the complex administered to it. In another embodiment, the NMR signal effecting amount of the complex is that amount which in addition to changing the relaxation times of the NMR signals in the host, will also change such relaxation times sufficiently so that sharper lines of definition or higher contrast is obtained between those parts of the host that have and have not been administered the complex.

The relaxation time $T_1$ (called the spin-lattice) measures the rate at which magnetic energy is transferred from the resonance nuclei to all other energetic degrees of freedom excluding other resonance nuclei. The relaxation time $T_2$ (spin-spin) measures the rate of magnetization transfer to other resonance nuclei.

Another parameter which can be measured is the density $\rho$ of the protons in the medium. As a first approximation, it represents the quantity of free water contained in the sample.

The image by nuclear magnetic resonance represented the distribution of these parameters $\rho$, $T_1$, $T_2$ or their combination. The contrast between a given tissue and the adjacent tissues increases as a function of the tissues containing more or less water or mobile protons and differing relaxation times. It is also possible to modify the contrast by varying one or more of these parameters (experimentally echoes of spins aiding the function of $T_2$, or reversal-recovery of the magnetization permitting the local measurement of $T_1$). Experience has shown that it was of greater interest to modify the relaxation time to improve the contrast of the image which can be accomplished, for example, with the contrast enhancing agents provided herein. The density of the protons (in practice those of water and lipids) varies little between individual organs and often less between normal and pathological tissues. However, the relaxation characteristics are dependent on a larger number of factors (microscopic dynamics of the molecules, chemical exchange, paramagnetic disturbances, etc.) which are much more variable.

A detailed discussion of NMR and theoretical considerations in selecting the appropriate parameters for diagnostic analysis, e.g. MRI, is rendered in U.S. Pat. No. 4,749,560 which is incorporated herein by reference. X-ray image analysis, ultrasonic diagnosis, scintiqraphic image analysis and radiotherapy utilizing the complexes of the invention are all conducted in accordance with well-established techniques known to those of ordinary skill in the art.

Moreover, the method of diagnostic analysis of the invention allows tissue or organ-specific diagnostic analysis to be achieved. For example, the contrast enhancing agents can exhibit organ and tissue specificity, e.g. biodifferental distribution, such as in myocardial tissue when the complexes of the invention are lipophilic in nature.

The complexes of the invention may be administered to a host as a pharmaceutical composition in a contrast-enhancing amount. The pharmaceutical compositions contain a contrast-enhancing dosage of the contrast agents according to the invention together with a nontoxic pharmaceutically acceptable carrier, adjuvant or vehicle. The compositions can be administered by well-known routes including oral, intravenous (if soluble), intramuscular, intranasal, intradermal, subcutaneous, parenteral, enteral and the like. Depending on the route of administration, the pharmaceutical composition may require protective coatings.

The pharmaceutical forms suitable for injectable use includes sterile aqueous solutions or dispersions and sterile powders for the extemporaneous preparation of sterile injectable solutions or dispersions. In all cases the ultimate solution form must be sterile and fluid. Typical carriers include a solvent or dispersion medium containing, for example, water, buffered aqueous solutions (i.e. biocompatable buffers), ethanol, polyol (glycerol, propylene glycol, polyethylene glycol, and the like), suitable mixtures thereof, surfactants or vegetable oils. Sterilization can be accomplished by any art recognized technique, including but not limited to, addition of antibacterial or antifungal agents, for example, paraben, chlorobutanol, phenol, sorbic acid, thimerosal, and the like. Further, isotonic agents, such as sugars or sodium chloride may be incorporated in the subject compositions.

Production of sterile injectable solutions containing the subject contrast agent is accomplished by incorporating these agents in the required amount in the appropriate solvent with various ingredients enumerated above, as required, followed by sterilization, preferably filter sterilization. To obtain a sterile powder, the above solutions are vacuum-dried or freeze-dried as necessary.

Solid dosage forms for oral administration may include capsules, tablets, pills, powders, granules and gels. In such solid dosage forms, the active compound may be admixed with at least one inert diluent such as sucrose, lactose or starch. Such dosage forms may also comprise, as in normal practice, additional substances other than inert diluent, e.g. lubricating agents such as magnesium stearate. In the case of capsules, tablets and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluent commonly used in the art, such as water. Such compositions may also comprise adjuvants, such as wetting agents, emulsifying and suspending agents, and sweetening, flavoring, and perfuming agents.

The contrast agents of the inventions are thus compounded for convenient and effective administration in pharmaceutically effective amounts with a suitable pharmaceutically acceptable carrier, adjuvant or vehicle in a dosage which effects contrast enhancement. These amounts are preferably about 1 µmol to 1 mol of the contrast agent per liter and/or administered in doses of about 0.001 to 5 mmol/kg body weight. Preferred compositions provide effective dosages of contrast agents in the range of about 0.001-5 mmol/kg for NMR diagnostics, preferably about 0.005-0.5 mmol/kg; in the range of about 0.1-5 mmol/kg for X-ray diagnostics; and in the range of about 0.1-5 mmol/kg for ultrasound diagnostics. For scintigraphic diagnostics, the dose of the contrast agent should generally be lower than for NMR diagnostics, e.g. MRI. For radiotherapy, conventional doses known to those of ordinary skill in the art can be used.

As used herein, a pharmaceutically acceptable carrier, adjuvant or vehicle includes any and all solvents, dispersion media, coatings, antibacterial and antifungal agents, isotonic agents, and the like. The use of such media and agents are well known in the art.

Contemplated equivalents of the general formulas set forth above for the compounds and derivatives as well as the intermediates are compounds otherwise corresponding thereto and having the same general properties such as tautomers of the compounds and such as wherein one or more of the various R groups are simple variations of the substituents as defined therein, e.g., wherein R is a higher alkyl group than that indicated, or where the tosyl groups are other nitrogen or oxygen protecting groups or wherein the O-tosyl is a halide. Anions having a charge other than 1, e.g., carbonate, phosphate, and hydrogen phosphate, can be used instead of anions having a charge of 1, so long as they do not adversely affect the overall activity of the complex. However, using anions having a charge other than 1 will result in a slight modification of the general formula for the complex set forth above. In addition, where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLES

All reagents were used as received without purification unless otherwise indicated. All NMR spectra were obtained on a Varian VXR-300 or VXR-400 nuclear magnetic resonance spectrometer. Qualitative and quantitative mass spectroscopy was run on a Finigan MAT90, a Finigan 4500 and a VG40-250T using m-nitrobenzyl alcohol (NBA), m-nitrobenzyl alcohol/LiCl (NBA–Li). Melting points (mp) are uncorrected.

The following abbreviations relating to amino acids and their protective groups are in accordance with the recommendation by IUPAC-IUB Commission on Biochemical Nomenclature (*Biochemistry* 1972, 11, 1726) and common usage.

| | |
|---|---|
| Ala | L-Alanine |
| DAla | D-Alanine |
| Gly | Glycine |
| Ser | L-Serine |
| DSer | D-Serine |
| Bzl | Benzyl |
| Boc | tert-Butoxycarbonyl |
| Et | Ethyl |
| TFA | Trifluoroacetic acid |
| DMF | Dimethylformamide |
| HOBT•H$_2$O | 1-Hydroxy-(1H)-benzotriazole monohydrate |
| EDC•HCl | 1-(3-Dimethylaminopropyl)-3-ethylcarbodiimide hydrochloride |
| TEA | Triethylamine |
| DMSO | Dimethylsulfoxide |
| THF | Tetrahydrofuran |
| DPPA | Diphenylphosphoryl azide |

*The abbreviation Cyc represents 1,2-cyclohexanediamine (stereochemistry, i.e. R,R or S,S, is indicated as such). This allows three letter code peptide nomenclature to be used in pseudopeptides containing the 1,2-cyclohexane diamine "residue".

Example 1

A. Synthesis of N-(p-toluenesulfonyl)-(R,R)-1,2-diaminocyclohexane

To a stirred solution of (R,R)-1,2-diaminocyclohexane (300 g, 2.63 mole) in CH$_2$Cl$_2$ (5.00 l) at −10° C. was added a solution of p-toluenesulfonylchloride (209 g, 1.10 mole) in CH$_2$Cl$_2$ (5.00 l) dropwise over a 7 h period, maintaining the temp at −5 to −10° C. The mixture was allowed to warm to room temp while stirring overnight. The mixture was concentrated in vacuo to a volume of 3 l and the white solid was removed by filtration. The solution was then washed with H$_2$O (10×1 l) and was dried over MgSO$_4$. Removal of the solvent in vacuo gave 286 g (97.5% yield) of the product as a yellow crystalline solid: $^1$H NMR (CDCl$_3$) δ 0.98-1.27 (m, 4H), 1.54-1.66 (m, 2H), 1.81-1.93 (m, 2H), 2.34 (dt, J=4.0, 10.7 Hz, 1H), 2.42 (s, 3H), 2.62 (dt, J=4.2, 9.9 Hz, 1H), 7.29 (d, J=8.1 Hz, 2H), 7.77 (d, J=8.3 Hz, 2H); MS (LRFAB-DTT-DTE) m/z 269 [M+H]$^+$.

B. Synthesis of N-(p-toluenesulfonyl)-N'-(Boc)-(R,R)-1,2-diaminocyclohexane To a stirred solution of N-(p-toluenesulfonyl)-(R,R)-1,2-diaminocyclohexane prepared as in Example 1A (256 g, 0.955 mole) in THF (1.15 l) was added a 1 N solution of aqueous NaOH (1.15 l, 1.15 mole). Di-t-butyldicarbonate (229 g, 1.05 mole) was then added and the resulting mixture was stirred overnight. The layers were separated and the aqueous layer was adjusted to pH 2 with 1 N HCl and saturated with NaCl. The aqueous solution was then extracted with CH$_2$Cl$_2$ (2×500 mL) and the extracts and THF layer were combined and dried over MgSO$_4$. The solvent was removed in vacuo to give a yellow solid. The crude product was purified by crystallization from a THF-ether-hexanes mixture to give 310 g (88.1% yield) of the product as a white crystalline solid: mp: 137-139° C.; $^1$H NMR (CDCl$_3$) δ 1.04-1.28 (m, 4H), 1.44 (s, 9H), 1.61-1.69 (m, 2H), 1.94-2.01 (m, 2H), 2.43 (s, 3H), 2.86 (brs, 1H), 3.30 (br d, J=9.6 Hz, 1H), 4.37 (br d, J=6.7 Hz, 1H), 5.48 (br d, J=4.6 Hz, 1H), 7.27 (d, J=9.7 Hz, 2H), 7.73 (d, J=8.1 Hz, 2H); MS (LRFAB, NBA–Li) m/z 375 [M+Li]$^+$.

C. Synthesis of Boc-(R,R)-Cyc(Ts)-gly-OMe

To a stirred solution of N-(p-toluenesulfonyl)-N'-(Boc)-(R,R)-1,2-diaminocyclohexane prepared as in Example 1B (310 g, 0.841 mole) in anhydrous DMF (3.11 l) at 0° C. was added NaH (37.4 g-60% in oil, 0.934 mole) in portions and the resulting mixture was stirred for 30 min. Methyl bromoacetate (142 g, 0.925 mole) was then added dropwise over 45 min and the mixture was allowed to warm to room temp while stirring overnight. After stirring for 17 h, the solvent was removed in vacuo and the residue was dissolved in ethyl acetate (3 l) and H$_2$O (1 l). The ethyl acetate solution was washed with saturated NaHCO$_3$ (1 l), saturated NaCl (500 mL) and was dried over MgSO$_4$. The solvent was removed in vacuo and the resulting oil was dissolved in ether. Crystallization by the addition of hexanes gave 364 g (98% yield) of the product (TLC (98:2 CHCl$_3$-MeOH/silica gel/UV detn) showed that the product contained about 5% starting material) as colorless needles: mp of pure sample 151-2° C.; $^1$H NMR (CDCl$_3$) δ 1.11-1.22 (m, 4H), 1.45 (s, 9H), 1.64-1.70 (m, 3H), 2.16-2.19 (m, 1H), 2.43 (s, 3H), 3.34-3.40 (m, 2H), 3.68 (s, 3H), 4.06 (ABq, J=18.5 Hz, Δv=155 Hz, 2H), 4.77 (br s 1H), 7.30 (d, J=8.3 Hz, 2H), 7.82 (d, J=8.3 Hz, 2H); MS (LRFAB, DTT-DTE) m/z 441 [M+H]$^+$.

D. Synthesis of Boc-(R,R)-Cyc-(Ts)-Gly-OH

To a stirred solution of impure Boc-(R,R)-Cyc(Ts)-Gly-OMe prepared as in Example 1C (217 g, 0.492 mole) in MeOH (1.05 l) was slowly added a 2.5N solution of aqueous NaOH (295 mL, 0.737 mole) and the resulting solution was stirred for 2 h. The solvent was removed in vacuo and the residue was dissolved in H$_2$O (1.5 l). The solution was filtered to remove a small amount of solid and was washed with ether (7×1 l) to remove the impurity (compound 1B) which upon drying of the combined washes over MgSO$_4$ and removal of the solvent in vacuo resulted in recovery of 8.37 g. The pH of the aqueous solution was then adjusted to 2 with 1 N HCl and the product was extracted with ethyl acetate (3×1 l). The extracts were combined, washed with saturated NaCl (500 mL) and dried over MgSO$_4$. The solvent was removed in vacuo and the residual ethyl acetate removed by coevaporation with ether (500 mL) and then CH$_2$Cl$_2$ (500 mL) to give 205 g (97.6% yield) of the product as a white foam: $^1$H NMR (CDCl$_3$) δ 1.15-1.22 (m, 4H), 1.48 (s, 9H), 1.55-1.68 (m, 3H), 2.12-2.15 (m, 1H), 2.43 (s, 3H), 3.41-3.49 (m, 2H), 3.97 (ABq, J=17.9 Hz, Δv=69.6 Hz, 2H), 4.79 (br s, 1H), 7.31 (d, J=8.1 Hz, 2H), 7.77 (d, J=8.3 Hz, 2H), 8.81 (br s, 1H); MS (LRFAB, NBA-Li) m/z 433 [M+Li]$^+$.

E. Synthesis of Boc-(R,R)-Cyc(Ts)-Gly-Gly-OEt

To Boc-(R,R)-Cyc(Ts)-Gly-OH (18.1 g, 43.1 mmol) in DMF (480 mL) was added HOBt.H$_2$O (7.92 g, 51.7 mmol) and EDC.HCl (9.91 g, 51.7 mmol) and the resulting mixture was allowed to stir for 20 min at RT. To this solution was added GlyOEt.HCl (6.0 g, 43.1 mmol) and TEA (7.2 mL, 51.7 mmol) and the resulting mixture was allowed to stir for 16 h thereafter. The DMF was evaporated and the residue was partitioned between water (250 mL) and EtOAc (400 mL). The EtOAc layer was separated and washed with 1N KHSO$_4$ (250 mL), water (250 mL), sat. NaHCO$_3$ (250 mL) and brine (250 mL) and dried (Na$_2$SO$_4$). Filtration and concentration afforded 21.9 g (99% yield) of pure product as a white foam: $^1$H NMR (DMSO-d$_6$) δ 1.00-1.10 (m, 1H), 1.19 (t, J=7.6 Hz, 3H), 1.38 (s, 9H), 1.50-1.56 (m, 3H), 1.75-1.84 (m, 1H), 2.38 (s, 3H), 3.30-3.40 (bs, 2H), 3.75-4.01 (complex m, 4H), 4.08 (q, J=7.6 Hz, 2H), 6.05 (bs, 1H), 7.32 (d, J=8.0 Hz, 2H), 7.77 (d, J=8.0 Hz, 2H), 8.32 (t, J=7.2 Hz, 1H); MS(HRFAB) m/z 518.2551 (M+Li)$^+$; 518.2512 calculatedd for C$_{24}$H$_{37}$N$_3$O$_7$SLi.

F. Synthesis of Cyc(Ts)-Gly-Gly-OEt TFA salt

To a solution of Boc-Cyc(Ts)-Gly-Gly-OEt (21.2 g, 41.4 mmol) in CH$_2$Cl$_2$ (180 mL) was added TFA (44 mL) and the resulting mixture was stirred at RT for 30 min. The solution was concentrated and the residue was dissolved in ether (50 mL) and precipitated with hexanes (500 mL). The solvents were decanted and the residue was washed with 10:1 hexanes/ether (500 mL). The final residue was dried thoroughly at high vacuum to afford 20.7 g (95% yield) of the product as a tan foam: $^1$H NMR (DMSO-d$_6$) δ 0.85-0.96 (m, 1H), 1.03-1.31 (complex m, 7H), 1.09 (t, J=7.6 Hz, 3H), 2.00 (m, 1H), 2.39 (s, 3H), 3.02 (bs, 1H), 3.62 (m, 1H), 3.82-4.05 (m, 4H), 4.10 (q, J=7.6, 2H), 7.41 (d, J=8.0 Hz, 2H), 7.67 (d, J=8.0 Hz, 2H), 8.25 (bs, 3H), 9.09 (t, J=5.63 Hz, 1H). MS(HRFAB) m/z 418.1990 (M−TFA+Li)$^+$; 418.1988 calculated for C$_{19}$H$_{29}$N$_3$O$_5$S.

G. Synthesis of Boc-Orn(Z)-Cyc(Ts)-Gly-Gly-OEt

To Boc-Orn(Z)-OH (8.37 g, 22.8 mmol) in DMF (200 mL) was added HOBt.H$_2$O (4.29 g, 27.4 mmol) and EDC.HCl (5.25 g, 27.4 mmol) and the resulting solution was stirred for 20 min at RT. To this solution was added Cyc(Ts)-Gly-Gly-OEt TFA salt (12.0 g, 22.8 mmol) and TEA (3.82 mL, 27.4 mmol) and stirring was maintained for 16 h thereafter. The DMF was evaporated and the residue was partitioned between water (200 mL) and EtOAc (250 mL). The ETOAc layer was separated and washed with 1N KHSO$_4$ (150 mL), water (150 mL), sat. NaHCO$_3$ (150 mL) and brine (150 mL) and dried (MgSO$_4$). Filtration and concentration afforded 15.1 g (87% yield) of the product as a white foam: $^1$H NMR (DMSO-d$_6$) δ 1.00-1.94 (complex m, 12H), 1.15 (t, J=7.4 Hz, 3H), 2.38 (s, 3H), 2.98 (bs, 2H), 3.30-3.46 (m, 2H), 3.70-3.82 (m, 4H), 3.90 4.02 (m, 1H), 4.05 (t, J=7.4 Hz, 2H), 5.00 (s, 2H), 6.43 (m, 1H), 7.17 (m, 1H), 7.20-7.37 (m, 8H), 7.78 (m, 2H), 8.30 (bs, 1H); MS(LRFAB, NBA+HCl) m/z 760 (M+H)$^+$.

H. Synthesis of Orn(Z)-Cyc(Ts)-Gly-Gly-OEt TFA salt

To a solution of Boc-Orn(Z)-Cyc(Ts)-Gly-Gly-OEt (14.5 g, 19.1 mmol) in CH$_2$Cl$_2$ (120 mL) was added TFA (30 mL) and the resulting solution was stirred at RT for 30 min. The solution was evaporated and the residue was triturated with ether (100 mL). The ether was decanted and the residue was dried thoroughly at high vacuum to afford 15.5 g (>100% yield, contains TFA) of the product as an orange foam: $^1$H NMR (DMSO-d$_6$) δ 0.97-1.93 (complex m, 12H), 1.16 (t, J=7.4 Hz, 3H), 2.38 (s, 3H), 2.98 (bs, 2H), 3.31-3.50 (m, 2H), 3.71-3.91 (m, 4H), 3.97-4.04 (m, 1H), 4.08 (q, J=7.4 Hz, 2H), 5.00 (s, 2H), 7.23-7.39 (m, 8H), 7.77-7.81 (m, 2H), 8.18 (bs, 3H), 8.41 (bs, 1H); MS(LRFAB, NBA+HCl) m/z 660 (M−TFA)$^+$.

I. Synthesis of Boc-Gly-Orn(Z)-Cyc(Ts)-Gly-Gly-OEt

To a solution of Boc-Gly-OH (3.36 g, 19.2 mmol) in DMF (220 mL) was added HOBt.H$_2$O (3.52 g, 23.0 mmol) and EDC.HCl (4.41 g, 23.0 mmol) and the resulting solution was stirred for 20 min at RT. To this solution was added Orn(Z)-Cyc(Ts)-Gly-Gly-OEt TFA salt (14.8 g, 19.2 mmol) and TEA (3.20 mL, 23.0 mmol) and stirring was maintained for 12 h thereafter. The DMF was evaporated and the residue was partitioned between water (200 mL) and EtOAc (350 mL). The layers were separated and the EtOAc layer was washed with 1N KHSO$_4$ (150 mL), water (150 mL), sat. NaHCO$_3$ (150 mL) and brine (150 mL) and dried (MgSO$_4$). Filtration and concentration afforded 13.7 g (87% yield) of the product as a white foam: $^1$H NMR (DMSO-d$_6$) δ 0.96-1.10 (m, 2H), 1.17 (t, J=7.4 Hz, 3H), 1.38 (s, 9H), 1.35-2.00 (complex m, 10H), 2.97 (m, 2H), 3.60 (bs, 2H), 3.67-3.84 (m, 4H), 3.93-4.03 (m, 3H), 4.06 (q, J=7.4 Hz, 2H), 6.92 (bs, 1H), 7.19 (m, 1H), 7.24-7.37 (m, 7H), 7.60 (d, J=8.3 Hz, 1H), 7.76 (m, 2H), 7.38 (bs, 1H). MS(LRFAB, NBA+Li)$^+$ m/z 823 (M+Li)$^+$.

J. Synthesis of Boc-Gly-Orn(Z)-Cyc(Ts)-Gly-Gly-OH

To a solution of Boc-Gly-Orn(Z)-Cyc(Ts)-Gly-Gly-OEt (13.3 g, 16.3 mmol) in methanol (100 mL) was added 1 N NaOH (25 mL). The resulting mixture was stirred at RT and monitored by TLC. After 2 h the reaction was complete. The methanol was evaporated and water (50 mL) was added to the residue. This aqueous phase was washed with EtOAc (2×100 mL) and the EtOAc layers were discarded. The pH was lowered to 3.5 with 1N KHSO$_4$ and the aqueous phase was extracted with EtOAc (3×100 mL). The combined EtOAc layers were dried (MgSO$_4$), filtered and concentrated to afforded 11.7 g (91% yield) of the product as a white foam: $^1$H NMR (CDCl$_3$) δ 0.98-1.25 (m, 2H), 1.38 (s, 9H), 1.40-1.92 (m, 10H), 2.38 (s, 3H), 2.97 (m, 2H), 3.62 (bs, 2H), 3.75-3.85 (m, 3H), 3.95-4.05 (m, 2H), 5.01 (s, 2H), 6.96 (bs, 1H), 7.28 (m, 1H), 7.25-7.38 (m, 7H), 7.61 (d, J=8.4 Hz, 1H), 7.78 (m, 2H), 8.25 (bs, 1H).

K. Synthesis of Gly-Orn(Z)-Cyc(Ts)-Gly-Gly-OH TFA salt

To a solution of Boc-Gly-Orn(Z)-Cyc(Ts)-Gly-Gly-OH (11.2 g, 14.3 mmol) in CH$_2$Cl$_2$ (100 mL) was added TFA (24 mL) and the resulting solution was stirred for 30 min at RT. The solution was concentrated and triturated with ethyl ether (500 mL). Filtration of afforded 11.3 g (99% yield) of the product as a white powder: $^1$H NMR (DMSO-d$_6$) δ 0.95-1.98 (complex m, 12H), 2.39 (s, 3H), 3.01 (m, 2H), 3.38 (m, 1H), 3.65-4.10 (complex m, 7H), 4.18 (q, J=7.4 Hz, 1H), 5.02 (s, 2H), 7.24-7.40 (m, 9H), 7.77-7.85 (m, 2H), 8.13 (bs, 3H), 8.31 (bs, 1H), 8.42 (d, J=8.3 Hz, 1H); MS(HRFAB) 689.2953 (M−TFA)$^+$; 689.2969 calculated for C$_{32}$H$_{45}$N$_6$O$_9$S.

L. Synthesis of cyclo-(Gly-Orn(Z)-Cyc(Ts)-Gly-Gly-)

A solution of Gly-Orn(Z)-Cyc(Ts)-Gly-Gly-OH TFA salt (5.0 g, 6.23 mmol) in dry degassed DMF (1520 mL) was treated with TEA (1.74 mL, 12.5 mmol) and cooled to −40° C. DPPA (1.64 mL, 7.60 mmol was added dropwise over 10 min and the reaction was stirred at −40° C. for 3 hr thereafter. After this time the reaction was place in a −2° C. bath and allowed to stand at this temperature for 16 h thereafter. Water (1520 mL) was added and the resulting solution was stirred with mixed bed ion-exchange resin (750 g) for 6 h at RT. The resin was filtered and the solution was concentrated to a volume of −100 mL (DMF). The addition of ethyl ether (500 mL) produced a solid residue which was redissolved in methanol (100 mL) and again precipitated by the addition of ethyl ether (500 mL). Filtration afforded 3.26 g (78% yield) of product as a white powder: $^1$H NMR (CDCl$_3$) δ 0.96-2.10 (complex m, 14H), 2.37 (bs, 3H), 2.68-3.05 (m, 3H), 3.42-3.90 (complex m, 8H), 4.14 (m, 1H), 4.20 (m, 1H), 4.97-5.08 (m, 3H), 6.42 (d, J=8.4 Hz, 1H), 7.19 (d, J=8.0 Hz, 1H), 7.20-7.39 (m, 7H), 7.65-7.78 (m, 2H), 9.15 (bs, 1H), 9.22 (bs, 1H); MS(HRFAB) m/z 671.2842 (M+H)$^+$; 671.2863 calculated for C$_{32}$H$_{43}$N$_6$O$_8$S.

M. Synthesis of cyclo-(Gly-Orn-Cyc(Ts)-Gly-Gly-)

To a solution of cyclo-(Gly-Orn(Z)-Cyc(Ts)-Gly-Gly-) (3.94 g, 5.90 mmol) in methanol (40 mL) was added Pd (black) (1.0 g) and ammonium formate (2.0 g). The reaction was refluxed for 2 h and allowed to cool. The mixture was filtered under Argon through a pad of celite and the filtrate was concentrated to afford 2.86 g (89% yield) of product as a white foam: $^1$H NMR (DMSO-d$_6$) δ 0.94-2.22 (complex m, 12H), 2.39 (s, 3H), 2.55-2.95 (m, 7H), 3.42-3.89 (complex m, 9H), 4.11 (m, 1H), 4.39 (m, 1H), 6.43 (d, J=8.4 Hz, 1H), 7.27 (d, J=9.3 Hz, 1H), 7.25-7.45 (m, 2H), 7.64-7.80 (m, 2H), 9.12-9.29 (m, 2H); MS (HRFAB) m/z 537.2511 (M+H)$^+$; 537.2495 calculated for C$_{24}$H$_{36}$N$_6$SO$_6$.

N. Synthesis of cyclo-(Gly-Orn(Lithocholyl)-Cyc(Ts)-Gly-Gly-)

To a solution of cyclo-(Gly-Orn-Cyc(Ts)-Gly-Gly-) (1.0 g, 1.9 mmol) in CHCl$_3$ (25 mL) was added lithocholic acid NHS active ester (881 mg, 1.9 mmol) and the resulting mixture was stirred for 16 h thereafter. Addition of ethyl ether (50 mL) produced a solid. Filtration afforded 946 mg (56% yield) of the product as a tan powder: $^1$H NMR (CD$_3$OD) δ 0.66 (m, 3H), 0.93 (bs, 6H), 0.94-2.37 (complex m, 48H), 2.43 (s, 3H), 2.80-4.60 (bm, 14H), 7.39 (bs, 2H), 7.80 (bs, 2H); MS (HR-FAB) m/z 895.5432 (M+H)$^+$; 895.5367 calculated for C$_{48}$H$_{75}$N$_6$O$_8$S.

O. Synthesis of 2,3-(R,R)-Cyclohexano-6-(S)-{3-(lithocholylamino)propyl}-1,4,7,10,13-penta-azaccloentadecane To a suspension of cyclo-(Gly-Orn(Lithocholyl)-Cyc(Ts)-Gly-Gly-) (2.70 g, 3.00 mmol) in THF (50 mL) was added lithium aluminum hydride (51.0 mL of a 1.0 M solution). The resulting mixture was refluxed for 16 h thereafter. The reaction mixture was cooled to ~−20° C. and quenched (cautiously) with 5% Na$_2$SO$_4$ (30 mL) followed by methanol (30 mL). This solution was stirred at RT for 1 h and concentrated to a dry powder. The powder was triturated with ethyl ether (3×200 mL) and filtered. The ether was concentrated and the oil was recrystallized from acetonitrile to afford 800 mg (40% yield) of product as a colorless oil $^1$H NMR (C$_6$D$_6$) δ 0.64 (s, 3H), 0.67 (s, 3H), 0.88 (d, J=3.0 Hz, 3H), 0.84-2.61 (complex m, 52H), 2.38-2.95 (complex m, 14H), 3.49 (m, 3H); $^{13}$C NMR (CDCl$_3$) δ 71.4, 63.1, 62.6, 61.8, 58.2, 56.5, 56.1, 51.5, 50.4, 50.1, 48.3, 47.9, 46.1, 45.7, 42.6, 42.1, 40.4, 40.1, 36.4, 35.8, 35.7, 35.6, 35.4, 34.5, 31.9, 31.7, 31.6, 30.8, 30.5, 29.4, 28.3, 27.2, 26.4, 26.2, 24.9, 24.2, 23.4, 20.8, 18.6, 12.0; MS(LRFAB, NBA+Li) m/z 677 (M+Li)$^+$.

P. Synthesis of [Manganese (II) dichloro 2,3-(R,R)-Cyclohexano-6-(S)-{3-(lithocholylamino)-propyl}-1,4,7,10,13-penta-azacclopentadecane]

2,3-(R,R)-Cyclohexano-6-(S)-{3-(lithocholylamino)propyl}-1,4,7,10,13-penta-azacclopentadecane prepared as in example 10 (547 mg, 0.817 mmol) was added to a hot anhydrous methanol solution (50 mL) containing manganese (II) chloride (103 mg, 0.818 mmol) under a dry nitrogen atmosphere. After refluxing for 2 h the solution was reduced to dryness and the residue was dissolved in a solvent mixture of THF (35 mL) and ethyl ether (5 mL) and filtered through a pad of celite. Concentration and trituration with ethyl ether afforded after filtration 512 mg (79% yield) of the complex as a white solid: FAB mass spectrum (NBA) m/z 760 [M−Cl]$^+$; Anal. Calculated. for C41H78N6OMnCl2: C, 61.79; H, 9.87; N, 10.55; Cl, 8.90. Found: C, 62.67; H, 9.84; N, 8.04; Cl, 8.29.

Example 2

Relaxivity measurements of the complex of Example 1 was determined.

Proton relaxation times (T$_1$) of the sample in 100 mM Hepes buffer, pH=7.4, at 40° C. were determined from a monoexponential curve fit obtained from inversion-recovery pulse sequences (180°-τ-90°) with a Bruker PC 120/125/10 VTs NMR process analyzer. The spectrometer was calibrated for each sample to assure accurate duration of 90° and 180° radio frequency pulses and appropriate magnetic field strength to match the 20 MHz system operating frequency. The relaxivity (R$_1$) was obtained from the slope of a plot of 1/T$_1$ versus the concentration of paramagnetic compound.

The relaxation time (T$_2$) of each sample in 100 mM Hepes buffer, pH=7.4, was measured at 40° C. using a Carr-Purcel-Meiboom-Gill pulse sequence on the same Bruker instrument. The relaxivity (R$_2$) was obtained from a plot of 1/T$_2$ versus the concentration of the paramagnetic compound.

The relaxivity of the complex of Example 1 is as follows: R$_1$ (nM$^{-1}$sec$^{-1}$)=6.09 and R$_2$ (mM$^{-1}$sec$^{-1}$)=18.5.

That which is claimed is:

1. A compound which is complex represented by the

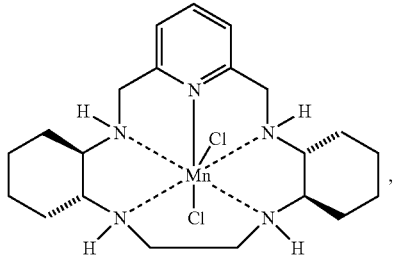

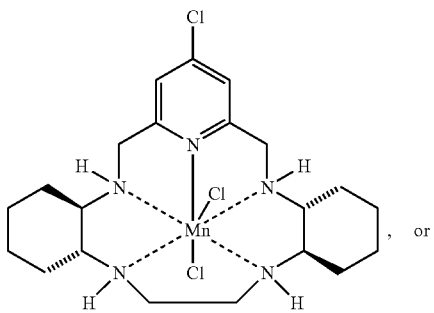, or

-continued

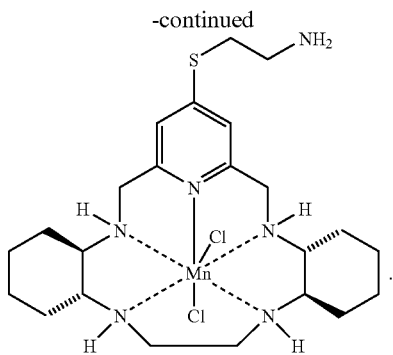.

wherein said biomolecule is independently selected from the group consisting of steroids, carbohydrates, fatty acids, amino acids, peptides, proteins, antibodies, vitamins, lipids, phospholipds, phosphates, phosphonates, nucleic acids, enzyme substrates, enzyme inhibitors and enzyme receptor substrates.

2. Compound of claim 1 wherein the biomolecule is a carbohydrate.

3. Compound of claim 2 wherein the biomolecule is a polysaccharide.

4. Compound of claim 3 wherein the biomolecule is a glycosaminoglycan.

5. Compound of claim 3 wherein the biomolecule is hyaluronic acid.

* * * * *